(12) United States Patent
Yamamoto et al.

(10) Patent No.: US 8,598,358 B2
(45) Date of Patent: Dec. 3, 2013

(54) SYNTHETIC INTERMEDIATE OF OXAZOLE COMPOUND AND METHOD FOR PRODUCING THE SAME

(75) Inventors: Akihiro Yamamoto, Osaka (JP); Koichi Shinhama, Osaka (JP); Nobuhisa Fujita, Osaka (JP); Shinji Aki, Osaka (JP); Shin Ogasawara, Osaka (JP); Naoto Utsumi, Osaka (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 13/574,546

(22) PCT Filed: Jan. 28, 2011

(86) PCT No.: PCT/JP2011/052307
§ 371 (c)(1),
(2), (4) Date: Jul. 20, 2012

(87) PCT Pub. No.: WO2011/093529
PCT Pub. Date: Aug. 4, 2011

(65) Prior Publication Data
US 2012/0302757 A1   Nov. 29, 2012

(30) Foreign Application Priority Data
Jan. 29, 2010   (JP) .................................. 2010-019289

(51) Int. Cl.
| C07D 211/46 | (2006.01) |
| C07D 405/12 | (2006.01) |
| C07D 498/04 | (2006.01) |

(52) U.S. Cl.
USPC ............................ 546/209; 546/223; 546/240

(58) Field of Classification Search
None
See application file for complete search history.

(56) References Cited

U.S. PATENT DOCUMENTS

| 5,319,108 | A | 6/1994 | Ebata et al. |
| 8,344,148 | B2 * | 1/2013 | Tsubouchi et al. ........... 546/199 |
| 2006/0079697 | A1 | 4/2006 | Goto et al. |
| 2006/0094767 | A1 | 5/2006 | Tsubouchi et al. |
| 2008/0097107 | A1 | 4/2008 | Goto et al. |
| 2008/0200689 | A1 | 8/2008 | Goto et al. |
| 2012/0130082 | A1 | 5/2012 | Goto et al. |

FOREIGN PATENT DOCUMENTS

| JP | 2009-269859 A | 11/2009 |
| WO | 2004/033463 A1 | 4/2004 |
| WO | 2004/035547 A1 | 4/2004 |
| WO | 2008/140090 A1 | 11/2008 |

OTHER PUBLICATIONS

International Search Report for PCT/JP2011/052307 dated Apr. 6, 2011.
L. Djakovitch et al, Amination of aryl bromides catalysed by supported palladium, Journal of Organometallic Chemistry, vol. 592, 1999, pp. 225-234.
V. Levacher et al, Efficient preparation of polymer-supported enantiopure chiral aminoalcohols via phenolic spacers, Reactive Polymers, vol. 24, (1995) pp. 183-193.

* cited by examiner

*Primary Examiner* — Kamal Saeed
(74) *Attorney, Agent, or Firm* — Sughrue Mion, PLLC

(57) ABSTRACT

An object of the present invention is to provide a method for producing an oxazole compound in a high yield.
The object can be achieved by a compound represented by Formula (11):

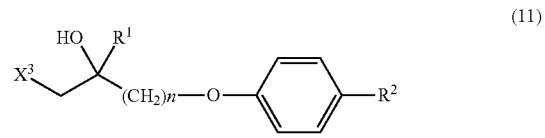

(11)

wherein $R^1$ is a hydrogen atom or lower-alkyl group;
$R^2$ is a 1-piperidyl group substituted at the 4-position with a substituent selected from
(A1a) a phenoxy group substituted on the phenyl moiety with one or more halogen-substituted lower-alkoxy groups,
(A1b) a phenoxy-substituted lower-alkyl group substituted on the phenyl moiety with one or more halogen-substituted lower-alkyl groups,
(A1c) a phenyl-substituted lower-alkoxy lower-alkyl group substituted on the phenyl moiety with halogen,
(A1d) a phenyl-substituted lower-alkyl group substituted on the phenyl moiety with one or more halogen-substituted lower-alkoxy groups,
(A1e) an amino group substituted with a phenyl group substituted with one or more halogen-substituted lower-alkoxy groups, and a lower-alkyl group, and
(A1f) a phenyl-substituted lower-alkoxy group substituted on the phenyl moiety with one or more halogen-substituted lower-alkoxy groups;
n is an integer from 1 to 6; and
$X^3$ is an organic sulfonyloxy group.

7 Claims, No Drawings

SYNTHETIC INTERMEDIATE OF OXAZOLE COMPOUND AND METHOD FOR PRODUCING THE SAME

CROSS REFERENCE TO RELATED APPLICATIONS

This application is a National Stage of International Application No. PCT/JP2011/052307 filed Jan. 28, 2011, claiming priority based on Japanese Patent Application No. 2010-019289 filed Jan. 29, 2010, the contents of all of which are incorporated herein by reference in their entirety.

TECHNICAL FIELD

The present invention relates to a synthetic intermediate of oxazole compound, and a method of production thereof.

BACKGROUND ART

A 2,3-dihydroimidazo[2,1-b]oxazole compound represented by Formula (1) below or a salt thereof is useful as an antitubercular agent (Patent Literatures 1, 2 and 3).

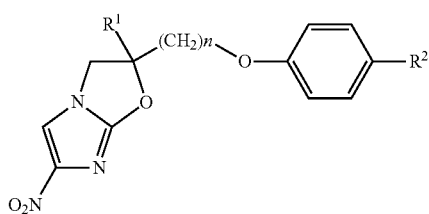

In Formula (1), $R^1$ is a hydrogen atom or lower-alkyl group;
$R^2$ is a 1-piperidyl group substituted at the 4-position with a substituent selected from
(A1a) a phenoxy group substituted on the phenyl moiety with one or more halogen-substituted lower-alkoxy groups,
(A1b) a phenoxy-substituted lower-alkyl group substituted on the phenyl moiety with one or more halogen-substituted lower-alkyl groups,
(A1c) a phenyl-substituted lower-alkoxy lower-alkyl group substituted on the phenyl moiety with halogen,
(A1d) a phenyl-substituted lower-alkyl group substituted on the phenyl moiety with one or more halogen-substituted lower-alkoxy groups,
(A1e) an amino group substituted with a phenyl group substituted with one or more halogen-substituted lower-alkoxy groups, and a lower-alkyl group, and
(A1f) a phenyl-substituted lower-alkoxy group substituted on the phenyl moiety with one or more halogen-substituted lower-alkoxy groups; and
n is an integer from 1 to 6.

These patent literatures disclose Reaction Schemes A and B below as the processes for producing the aforementioned 2,3-dihydroimidazo[2,1-b]oxazole compound.

Reaction Scheme A:

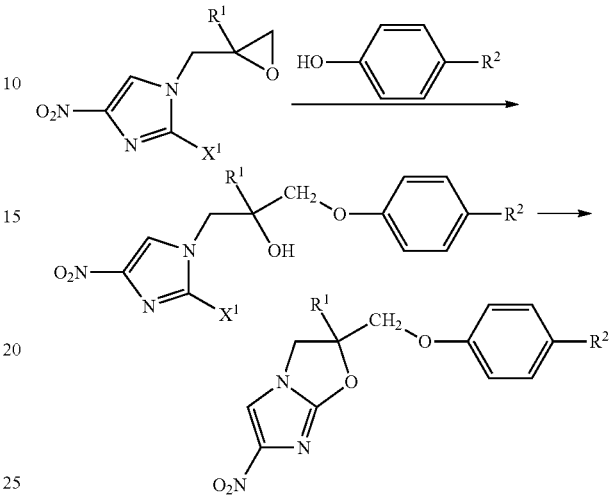

wherein $R^1$ is a hydrogen atom or lower-alkyl group; $R^2$ is a substituted piperidyl group or a substituted piperazinyl group; and $X^1$ is a halogen atom or a nitro group.

Reaction Scheme B:

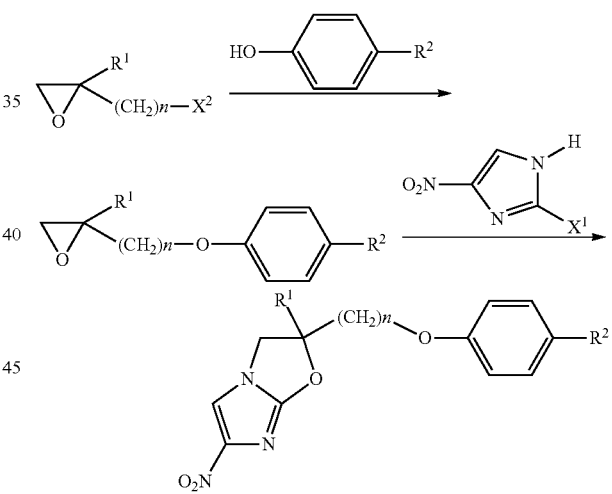

wherein $X^2$ is a halogen or a group causing a substitution reaction similar to that of a halogen; n is an integer from 1 to 6; and $R^1$, $R^2$ and $X^1$ are the same as in Reaction Scheme A.

An oxazole compound represented by Formula (1a):

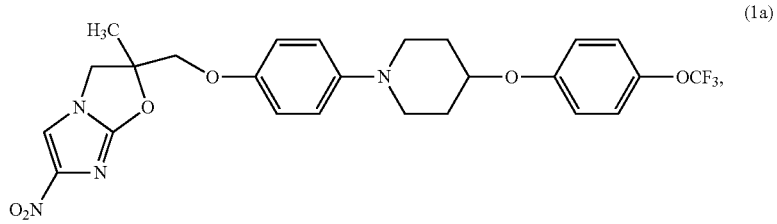 [SMILES: CC1(COc2ccc(N3CCC(Oc4ccc(OC(F)(F)F)cc4)CC3)cc2)Cn2cc([N+](=O)[O-])nc2O1]

i.e., 2-methyl-6-nitro-2-{4-[4-(4-trifluoromethoxyphenoxy)piperidin-1-yl]phenoxymethyl}-2,3-dihydroimidazo[2,1-b]oxazole (hereunder, this compound may be simply referred to as "Compound 1a") is produced, for example, by the method shown in the Reaction Scheme C below (Patent Literature 3). In this specification, the term "oxazole compound" means an oxazole derivative that encompasses compounds that contain an oxazole ring or an oxazoline ring (dihydrooxazole ring) in the molecule.

However, the aforementioned methods are unsatisfactory in terms of the yield of the objective compound. For example, the method of Reaction Scheme C allows the objective oxazole Compound (1a) to be obtained from Compound (2a) at a yield as low as 35.9%. Therefore, alternative methods for producing the compound in an industrially advantageous manner are desired.

Reaction Scheme C:

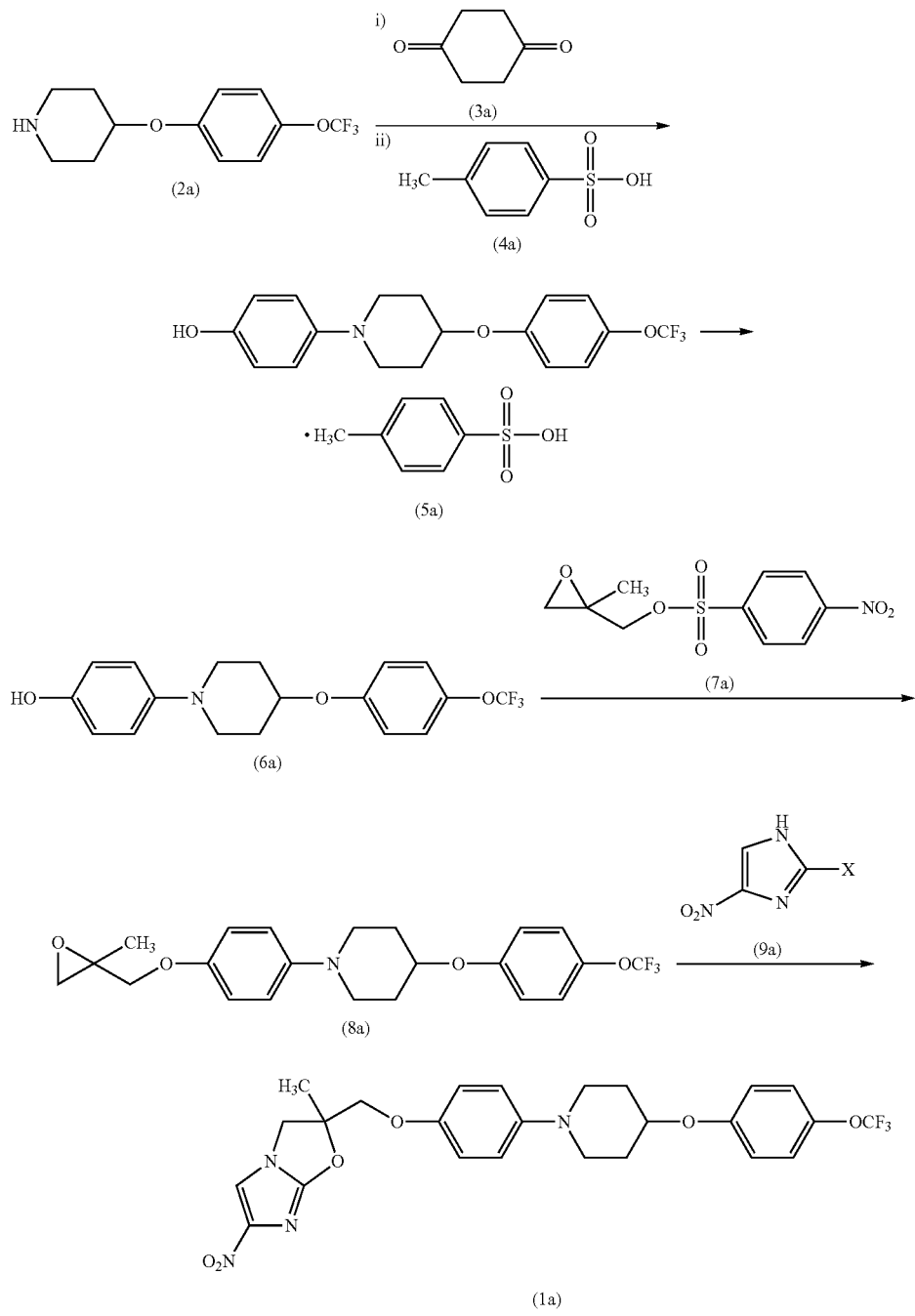

X: Cl, Br

CITATION LIST

Patent Literature

PTL 1: WO2004/033463
PTL 2: WO2004/035547
PTL 3: WO2008/140090

SUMMARY OF INVENTION

Technical Problem

An object of the present invention is to provide a novel synthetic intermediate that is usable for producing an oxazole compound represented by Formula (1) including Compound (1a) at a high yield and high purity (in particular, a high optical purity), and a method for producing the synthetic intermediate.

Solution to Problem

The present inventors conducted extensive research to achieve the above object, and found that the objective oxazole compound represented by Formula (1) can be produced at a high yield and high purity by using the compound described below as a synthetic intermediate, and a production method using the synthetic intermediate. The present invention has been accomplished according to these findings.

More specifically, the present invention provides the following aspects and the like.
Item 1.
A compound represented by Formula (11):

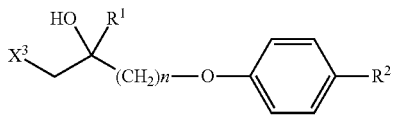

wherein $R^1$ is a hydrogen atom or lower-alkyl group;
$R^2$ is a 1-piperidyl group substituted at the 4-position with a substituent selected from
(A1a) a phenoxy group substituted on the phenyl moiety with one or more halogen-substituted lower-alkoxy groups,
(A1b) a phenoxy-substituted lower-alkyl group substituted on the phenyl moiety with one or more halogen-substituted lower-alkyl groups,
(A1c) a phenyl-substituted lower-alkoxy lower-alkyl group substituted on the phenyl moiety with halogen,
(A1d) a phenyl-substituted lower-alkyl group substituted on the phenyl moiety with one or more halogen-substituted lower-alkoxy groups,
(A1e) an amino group substituted with a phenyl group substituted with one or more halogen-substituted lower-alkoxy groups, and a lower-alkyl group, and
(A1f) a phenyl-substituted lower-alkoxy group substituted on the phenyl moiety with one or more halogen-substituted lower-alkoxy groups;
n is an integer from 1 to 6; and
$X^3$ is an organic sulfonyloxy group.
Item 2.
A method for producing the compound of Item 1,
the method comprising reacting a compound represented by Formula (10):

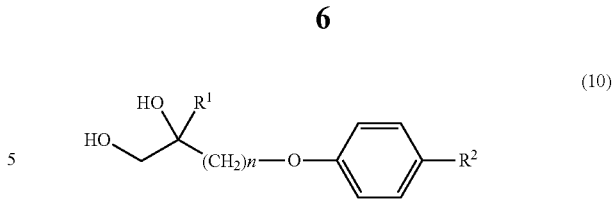

wherein $R^1$, $R^2$ and n are the same as in Item 1,
with an organic sulfonic acid.
Item 3.
A compound represented by Formula (10):

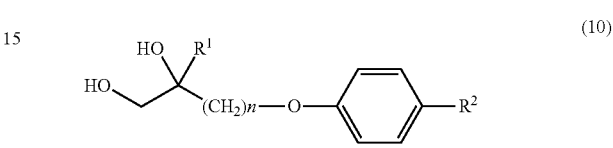

wherein $R^1$, $R^2$ and n are the same as in Item 1.
Item 4.
A method for producing the compound of Item 3,
the method comprising reacting a compound represented by Formula (9):

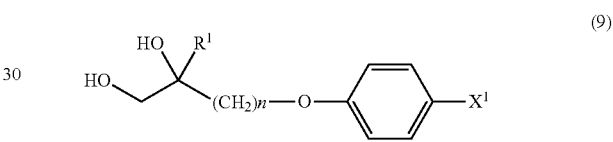

wherein $X^1$ is a leaving group, and $R^1$ and n are the same as in Item 1,
with a compound represented by Formula (2):

$$H-R^2 \quad (2)$$

wherein $R^2$ is the same as in Item 1.
Item 5.
A method for producing the compound of Item 3,
the method comprising reacting a compound represented by Formula (9):

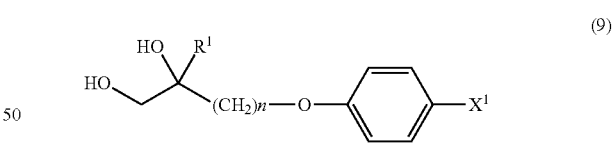

wherein $X^1$ is a leaving group, and $R^1$ and n are the same as defined in Item 1,
with a compound represented by Formula (9-i):

wherein $R^A$ is a lower-alkyl group or a phenyl group which may have a substituent or substituents; and $R^B$ is a hydrogen atom or a lower-alkyl group, $R^A$ and $R^B$ may form a cycloalkyl ring together with the carbon atom to which they are bonded, to obtain a compound represented by Formula (9-ii):

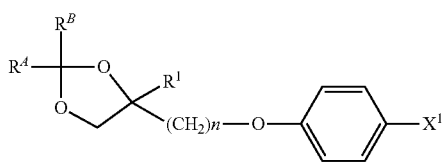

(9-ii)

wherein $R^1$, $X^1$, n, $R^A$ and $R^B$ are the same as the above, the compound represented by Formula (9-ii) is reacted with a compound represented by Formula (2):

H—$R^2$   (2)

wherein $R^2$ is the same as defined in Item 1,
to obtain a compound represented by Formula (9-iii):

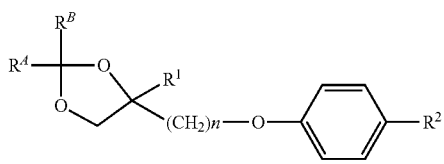

(9-iii)

wherein $R^1$, $R^2$, n, $R^A$ and $R^B$ are the same as the above, and subjecting the compound represented by Formula (9-iii) to deprotection.

Item 6.

A method for producing a compound represented by Formula (12):

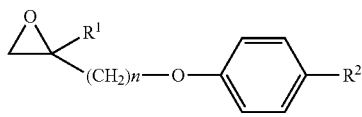

(12)

wherein $R^1$, $R^2$ and n are the same as in Item 1,
the method comprising subjecting the compound of Item 1 to an epoxidation reaction.

Item 7.

A method for producing a compound represented by Formula (1):

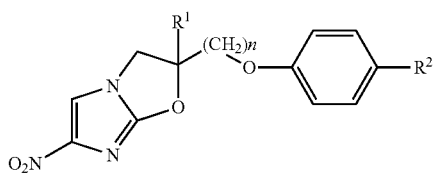

(1)

wherein $R^1$, $R^2$ and n are the same as in Item 1,
the method comprising the steps (a) to (c):

(a) subjecting the compound of Item 1 to an epoxidation reaction to prepare a compound represented by Formula (12):

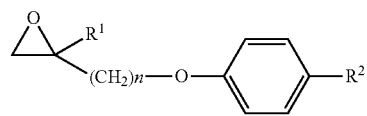

(12)

wherein $R^1$, $R^2$ and n are the same as in Item 1;

(b) reacting a compound represented by Formula (12) with a compound represented by Formula (8):

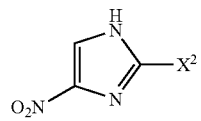

(8)

wherein $X^2$ is a halogen atom, to prepare a compound represented by Formula (13):

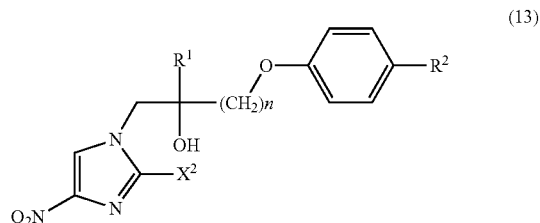

(13)

wherein $R^1$, $R^2$, $X^2$ and n are the same as described above; and (c) subjecting the compound represented by Formula (13) to a ring closure reaction to prepare the compound represented by Formula (1).

The present invention also provides the following method.

Item 7. A method for producing a compound represented by Formula (1):

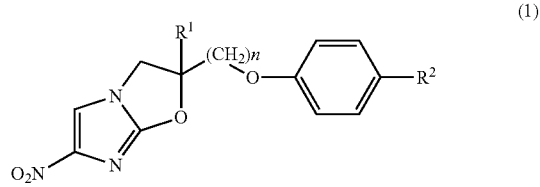

(1)

wherein $R^1$ is a hydrogen atom or lower-alkyl group;
$R^2$ is a 1-piperidyl group substituted at the 4-position with a substituent selected from (A1a) a phenoxy group substituted on the phenyl moiety with one or more halogen-substituted lower-alkoxy groups, (A1b) a phenoxy-substituted lower-alkyl group substituted on the phenyl moiety with one or more halogen-substituted lower-alkyl groups, (A1c) a phenyl-substituted lower-alkoxy lower-alkyl group substituted on the phenyl moiety with halogen, (A1d) a phenyl-substituted lower-alkyl group substituted on the phenyl moiety with one or more halogen-substituted lower-alkoxy groups, (A1e) an amino group substituted with a phenyl group substituted with one or more halogen-substituted lower-alkoxy groups, and a lower-alkyl group, and (A1f) a phenyl-substituted lower-alkoxy group substituted on the phenyl moiety with one or more halogen-substituted lower-alkoxy groups; and n is an integer from 1 to 6;

the method comprising the steps of (a) reacting a compound represented by Formula (9):

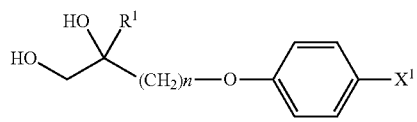
(9)

wherein $X^1$ is a leaving group, and $R^1$ and n are the same as in Item 1, with a compound represented by Formula (2):

(2)

wherein $R^2$ is the same as in Item 1, to prepare a compound represented by Formula (10):

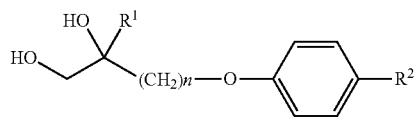
(10)

wherein $R^1$, $R^2$, and n are the same as the above;

(b) reacting the compound represented by Formula (10) with an organic sulfonic acid to prepare a compound represented by Formula (11):

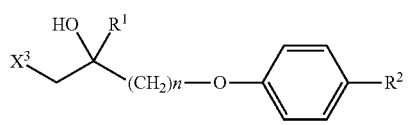
(11)

wherein $X^3$ is an organic sulfonyloxy group, and $R^1$, $R^2$, and n are the same as the above;

(c) subjecting the compound represented by Formula (11) to an epoxidation reaction to prepare a compound represented by Formula (12):

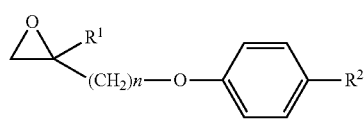
(12)

wherein $R^1$, $R^2$, and n are the same as the above;

(d) reacting the compound represented by Formula (12) with a compound represented by Formula (8):

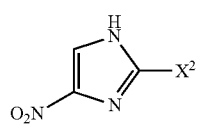
(8)

wherein $X^2$ is a halogen atom, to prepare a compound represented by Formula (13):

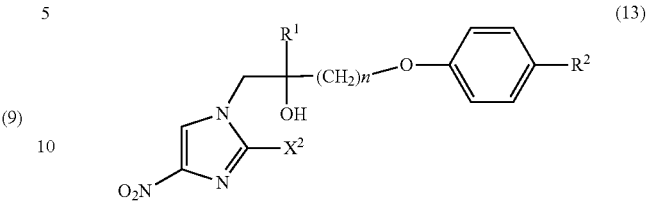
(13)

wherein $R^1$, $R^2$, $X^2$, and n are the same as the above; and (e) subjecting the compound represented by Formula (13) to a ring closure reaction to prepare a compound represented by Formula (1):

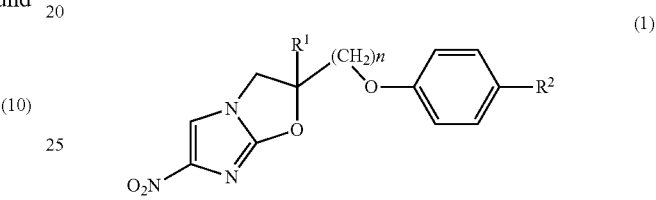
(1)

wherein $R^1$, $R^2$, and n are the same as the above.

Each term described in the present specification is specifically as follows.

In this specification, the term "room temperature" means a temperature, for example, within the range from 10° C. to 35° C.

The term "at the 4-position" of 1-piperidyl group means the position shown by the numeric character 4 below as generally understood by those having ordinary skill in art.

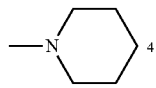

Each group described in the present specification is specifically as follows.

The halogen atoms (or halogen) include a fluorine atom, chlorine atom, bromine atom and iodine atom.

The lower-alkoxy groups include, for example, linear or branched alkoxy groups having 1 to 6 carbon atoms (preferably 1 to 4 carbon atoms). More specifically, they include methoxy, ethoxy, n-propoxy, isopropoxy, n-butoxy, isobutoxy, tert-butoxy, sec-butoxy, n-pentyloxy, 1-ethylpropoxy, isopentyloxy, neopentyloxy, n-hexyloxy, 1,2,2-trimethylpropoxy, 3,3-dimethylbutoxy, 2-ethylbutoxy, isohexyloxy and 3-methylpentyloxy groups.

The halogen-substituted lower-alkoxy groups include the lower-alkoxy groups as mentioned above substituted with 1 to 7, preferably 1 to 3, halogen atoms. More specifically, they include fluoromethoxy, difluoromethoxy, trifluoromethoxy, chloromethoxy, dichloromethoxy, trichloromethoxy, bromomethoxy, dibromomethoxy, dichlorofluoromethoxy, 2,2,2-trifluoroethoxy, pentafluoroethoxy, 2-chloroethoxy, 3,3,3-trifluoropropoxy, heptafluoropropoxy, heptafluoroisopropoxy, 3-chloropropoxy, 2-chloropropoxy, 3-bromopropoxy, 4,4,4-trifluorobutoxy, 4,4,4,3,3-pentafluorobutoxy, 4-chlorobutoxy, 4-bromobutoxy, 2-chlorobutoxy, 5,5,5-trifluoropentyloxy, 5-chloropentyloxy, 6,6,6-trifluorohexyloxy and 6-chlorohexyloxy groups.

The phenoxy groups substituted on the phenyl moiety with one or more halogen-substituted lower-alkoxy groups include, for example, phenoxy groups substituted on the phenyl moiety with one or more 1 to 3 (preferably 1) halogen-substituted lower-alkoxy groups as mentioned above.

The lower-alkyl groups include linear or branched alkyl groups having 1 to 6 carbon atoms (preferably 1 to 4 carbon atoms). More specifically, they include methyl, ethyl, n-propyl, isopropyl, n-butyl, isobutyl, tert-butyl, sec-butyl, n-pentyl, 1-ethylpropyl, isopentyl, neopentyl, n-hexyl, 1,2,2-trimethylpropyl, 3,3-dimethylbutyl, 2-ethylbutyl, isohexyl and 3-methylpentyl groups.

The halogen-substituted lower-alkyl groups include the lower-alkyl groups as mentioned above substituted with 1 to 7, preferably 1 to 3, halogen atoms. More specifically, they include fluoromethyl, difluoromethyl, trifluoromethyl, chloromethyl, dichloromethyl, trichloromethyl, bromomethyl, dibromomethyl, dichlorofluoromethyl, 2,2-difluoroethyl, 2,2,2-trifluoroethyl, pentafluoroethyl, 2-fluoroethyl, 2-chloroethyl, 3,3,3-trifluoropropyl, heptafluoropropyl, 2,2,3,3,3-pentafluoropropyl, heptafluoroisopropyl, 3-chloropropyl, 2-chloropropyl, 3-bromopropyl, 4,4,4-trifluorobutyl, 4,4,4,3,3-pentafluorobutyl, 4-chlorobutyl, 4-bromobutyl, 2-chlorobutyl, 5,5,5-trifluoropentyl, 5-chloropentyl, 6,6,6-trifluorohexyl and 6-chlorohexyl groups.

The phenoxy-substituted lower-alkyl groups are exemplified by the lower-alkyl groups as mentioned above substituted with one phenoxy group. More specifically, they include phenoxymethyl, 2-phenoxyethyl, 1-phenoxyethyl, 2-phenoxyethyl, 2-phenoxy-1-methylethyl, 2-phenoxy-1-ethylethyl, 3-phenoxypropyl and 4-phenoxybutyl groups.

The phenoxy-substituted lower-alkyl groups substituted on the phenyl moiety with one or more halogen-substituted lower-alkyl groups include, for example, the phenoxy-substituted lower-alkyl groups as mentioned above substituted with 1 to 3 (preferably 1) halogen-substituted lower-alkyl groups as mentioned above.

The lower-alkoxy lower-alkyl groups are exemplified by the lower-alkyl groups as mentioned above substituted with one lower-alkoxy group as mentioned above. More specifically, they include methoxymethyl, 2-methoxyethyl, 1-ethoxyethyl, 2-ethoxyethyl, 2-isobutoxyethyl, 2,2-dimethoxyethyl, 2-methoxy-1-methylethyl, 2-methoxy-1-ethylethyl, 3-methoxypropyl, 3-ethoxypropyl, 3-isobutoxypropyl, 3-n-butoxypropyl, 4-n-propoxybutyl, 1-methyl-3-isobutoxypropyl, 1,1-dimethyl-2-n-pentyloxyethyl, 5-n-hexyloxypentyl, 6-methoxyhexyl, 1-ethoxyisopropyl and 2-methyl-3-methoxypropyl groups.

The phenyl-substituted lower-alkoxy lower-alkyl groups are exemplified by the lower-alkoxy lower-alkyl groups as mentioned above substituted with one phenyl group on a lower-alkoxy group. More specifically, they include benzyloxymethyl, (2-phenylethoxy)methyl, (1-phenylethoxy)methyl, 3-(3-phenylpropoxy)propyl, 4-(4-phenylbutoxy)butyl, 5-(5-phenylpentyloxy)pentyl, 6-(6-phenylhexyloxy)hexyl, 1,1-dimethyl-(2-phenylethoxy)ethyl, 2-methyl-3-(3-phenylpropoxy)propyl, 2-benzyloxyethyl, 1-benzyloxyethyl, 3-benzyloxypropyl, 4-benzyloxybutyl, 5-benzyloxypentyl and 6-benzyloxyhexyl groups.

The phenyl-substituted lower-alkoxy lower-alkyl groups substituted on the phenyl moiety with halogen include, for example, the phenyl-substituted lower-alkoxy lower-alkyl groups as mentioned above having 1 to 7, more preferably 1 to 3 halogen atoms.

The phenyl-substituted lower-alkyl groups are exemplified by the lower-alkyl groups as mentioned above substituted with one phenyl group. More specifically, they include benzyl, 1-phenylethyl, 2-phenylethyl, 1-methyl-1-phenylethyl, 1,1-dimethyl-2-phenylethyl, 1,1-dimethyl-3-phenylpropyl, 3-phenylpropyl and 4-phenylbutyl groups.

The phenyl-substituted lower-alkyl groups substituted on the phenyl moiety with one or more halogen-substituted lower-alkoxy groups include, for example, the phenyl-substituted lower-alkyl groups as mentioned above substituted with 1 to 3 (preferably 1) halogen-substituted lower-alkoxy groups as mentioned above.

The phenyl groups substituted with one or more halogen-substituted lower-alkoxy groups include, for example, phenyl groups substituted with 1 to 3 (preferably 1) halogen-substituted lower-alkoxy groups as mentioned above. The phenyl groups substituted with one or more halogen-substituted lower-alkoxy groups include, for example, phenyl groups substituted with 1 to 3 (preferably 1) halogen-substituted lower-alkoxy groups.

The amino groups substituted with a phenyl group substituted with one or more halogen-substituted lower-alkoxy groups and a lower-alkyl group include, for example, amino groups substituted with one phenyl group substituted with one or more halogen-substituted lower-alkoxy groups as mentioned above and one lower-alkyl group as mentioned above.

The phenyl-substituted lower-alkoxy groups are exemplified by the lower-alkyl groups as mentioned above substituted with one phenyl group. More specifically, they include benzyloxy, 1-phenylethoxy, 2-phenylethoxy, 1-methyl-1-phenylethoxy, 1,1-dimethyl-2-phenylethoxy, 1,1-dimethyl-3-phenylpropoxy, 3-phenylpropoxy and 4-phenylbutoxy groups.

The phenyl-substituted lower-alkoxy groups substituted on the phenyl moiety with one or more halogen-substituted lower-alkoxy groups include, for example, the phenyl-substituted lower-alkoxy groups as mentioned above substituted with 1 to 3 (preferably 1) halogen-substituted lower-alkoxy groups as mentioned above.

A method for producing an oxazole compound represented by Formula (1), which is one aspect of the present invention, is explained below. Other aspects can also be understood by this explanation.

The method for producing the oxazole compound represented by Formula (1) of the present invention is schematically illustrated in the following Reaction Scheme D.

Reaction Scheme D:

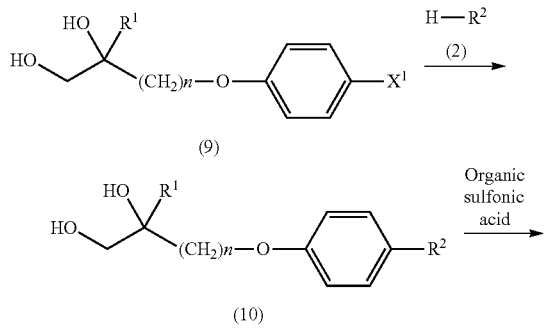

-continued

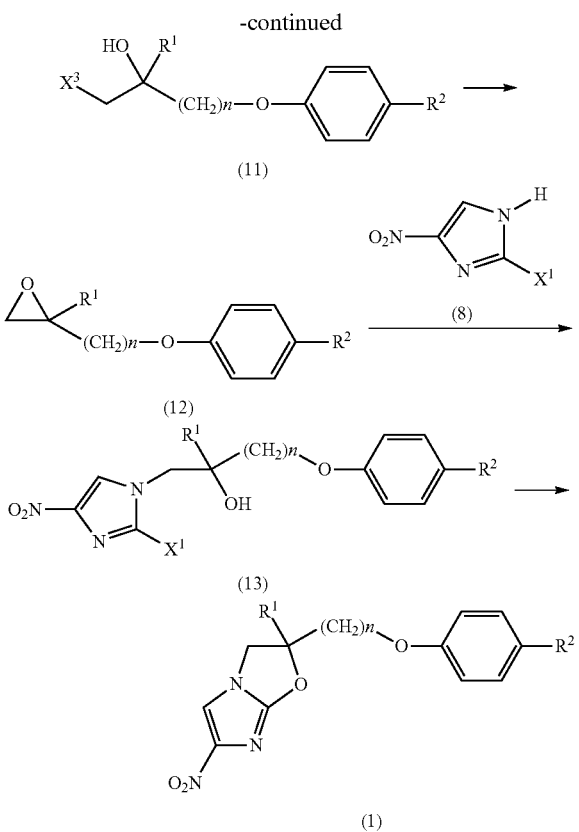

In Reaction Scheme D, $R^1$, $R^2$, $X^1$, $X^2$, $X^3$ and n are the same as the above.

One aspect of the method for producing the oxazole compound represented by Formula (1) comprises Steps 1 to 5 described below.

Step 1: Reacting a compound represented by Formula (9):

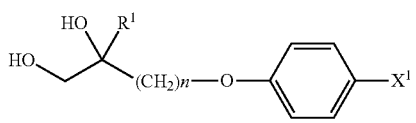

wherein $R^1$ is a hydrogen atom or lower-alkyl group, n is an integer from 1 to 6, and $X^1$ is a leaving group, with a compound represented by Formula (2):

H—$R^2$ (2)

wherein $R^2$ is a 1-piperidyl group substituted at the 4-position with a substituent selected from (A1a) a phenoxy group substituted on the phenyl moiety with one or more halogen-substituted lower-alkoxy groups, (A1b) a phenoxy-substituted lower-alkyl group substituted on the phenyl moiety with one or more halogen-substituted lower-alkyl groups, (A1c) a phenyl-substituted lower-alkoxy lower-alkyl group substituted on the phenyl moiety with halogen, (A1d) a phenyl-substituted lower-alkyl group substituted on the phenyl moiety with one or more halogen-substituted lower-alkoxy groups, (A1e) an amino group substituted with a phenyl group substituted with one or more halogen-substituted lower-alkoxy groups, and a lower-alkyl group, and (A1f) a phenyl-substituted lower-alkoxy group substituted on the phenyl moiety with one or more halogen-substituted lower-alkoxy groups, to prepare a compound represented by Formula (10):

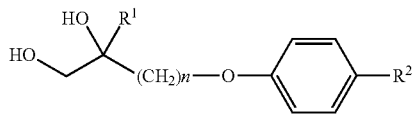

wherein $R^1$, $R^2$ and n are the same as the above.

Step 2: Reacting the compound represented by Formula (10) with an organic sulfonic acid to prepare a compound represented by Formula (11):

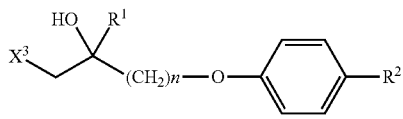

wherein $X^3$ is an organic sulfonyloxy group, and $R^1$, $R^2$ and n are the same as the above.

Step 3: Subjecting the compound represented by Formula (11) to an epoxidation reaction to prepare a compound represented by Formula (12):

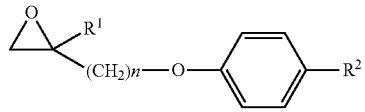

wherein $R^1$, $R^2$ and n are the same as the above.

Step 4: Reacting the compound represented by Formula (12) with a compound represented by Formula (8):

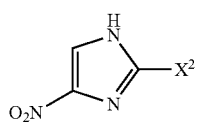

wherein $X^2$ is a halogen atom, to prepare a compound represented by Formula (13):

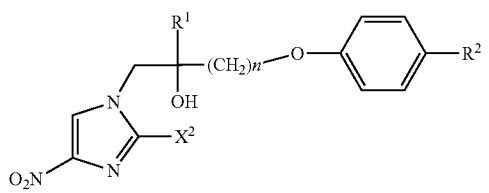

wherein $R^1$, $R^2$, $X^2$ and n are the same as the above.

Step 5: Subjecting the compound represented by Formula (13) to a ring closure reaction to prepare a compound represented by Formula (1):

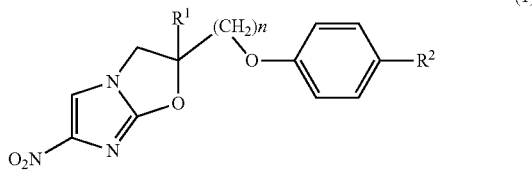

(1)

wherein $R^1$, $R^2$ and n are the same as the above.

Each step is explained in detail below.

<Step 1>

The compound represented by Formula (10) is prepared by reacting the compound represented by Formula (9) with the compound represented by Formula (2).

Examples of the leaving groups represented by $X^1$ in Formula (9) include a halogen atom, a halogen-substituted or unsubstituted lower alkanesulfonyloxy group, substituted or unsubstituted arylsulfonyloxy group, and the like. Among these, halogen atom is preferable. The halogen-substituted or unsubstituted lower alkanesulfonyloxy groups are specifically exemplified by linear or branched alkanesulfonyloxy groups having 1 to 6 carbon atoms, such as methanesulfonyloxy, ethanesulfonyloxy, n-propanesulfonyloxy, isopropanesulfonyloxy, n-butanesulfonyloxy, tert-butanesulfonyloxy, n-pentanesulfonyloxy, n-hexanesulfonyloxy, trifluoromethanesulfonyloxy, and 2,2,2-trifluoroethanesulfonyloxy groups.

The substituted or unsubstituted arylsulfonyloxy groups include, for example, phenylsulfonyloxy and naphthylsulfonyloxy groups which each may have, on the benzene ring, 1 to 3 substituents selected from the group consisting of linear or branched alkyl groups having 1 to 6 carbon atoms, linear or branched alkoxy groups having 1 to 6 carbon atoms, nitro groups and halogen atoms. The phenylsulfonyloxy groups which may have the substituent or substituents are specifically exemplified by phenylsulfonyloxy, 4-methylphenylsulfonyloxy, 2-methylphenylsulfonyloxy, 4-nitrophenylsulfonyloxy, 4-methoxyphenylsulfonyloxy, 2-nitrophenylsulfonyloxy and 3-chlorophenylsulfonyloxy groups. The naphthylsulfonyloxy groups are specifically exemplified by α-naphthylsulfonyloxy and β-naphthylsulfonyloxy groups.

The reaction of a compound represented by Formula (2) with a compound represented by Formula (9) is performed without a solvent or in an inert solvent, under the presence of a transition metal compound and a ligand, and under the presence of a basic compound or the absence thereof.

In this step, the use of a transition metal and a ligand is essential. They are combined and added as a catalyst to the reaction system. As for the addition method, the transition metal and ligand can be added to the reaction system separately, or a complex thereof may be added to the system.

Examples of transition metal compounds include compounds comprising 8 to 11 group elements. Preferable examples thereof include nickel compounds, palladium compounds and copper compounds. Among these, palladium compounds are the most preferable. The palladium compounds are not particularly limited, and examples thereof include tetravalent palladium compounds, such as sodium hexachloropalladium (IV) acid tetrahydrate and potassium hexachloropalladium (IV) acid; divalent palladium compounds, such as palladium (II) chloride, palladium (II) bromide, palladium (II) acetate, palladium (II) acetylacetonate, dichlorobis(benzonitrile)palladium (II), dichlorobis(triphenylphosphine)palladium (II) and dichloro(cycloocta-1,5-diene)palladium (II); zerovalent palladium compounds, such as tris(dibenzylideneacetone)dipalladium (0), chloroform complex of tris(dibenzylideneacetone)dipalladium (0) and tetrakis(triphenylphosphine)palladium (0); and the like. Among these, tris(dibenzylideneacetone)dipalladium (0) and chloroform complex of tris(dibenzylideneacetone)dipalladium (0) are preferable.

Examples of ligands include phosphines, N-heterocyclic carbenes and the like. The phosphines are not particularly limited and examples thereof include monodentate phosphines, such as triisopropylphosphine, tri-tert-butylphosphine, triphenylphosphine, tri-o-tolylphosphine, 2-(di-tert-butylphosphino)biphenyl, 2-di-tert-butylphosphino-2'-(N,N-dimethylamino)biphenyl, 2-di-tert-butylphosphino-2'-methylbiphenyl, 2-di-tert-butylphosphino-2',4',6'-triisopropyl-1,1'-biphenyl, 2-(dicyclohexylphosphino)biphenyl, 2-di-tert-butylphosphino-1,1'-binaphthyl, 2'-dicyclohexylphosphino-2,6-dimethoxy-3-sulfonato-1,1'-biphenyl hydrate sodium salt, 2-(dicyclohexylphosphino)-2'-(N,N-dimethylamino)biphenyl, 2-dicyclohexylphosphino-2',6'-di-i-propoxy-1,1'-biphenyl, 2-dicyclohexylphosphino-2'-methylbiphenyl, 2-(dicyclohexylphosphino)-2',4',6'-triisopropyl-1,1'-biphenyl, 2-diphenylphosphino-2'-(N,N-dimethylamino)biphenyl, 5-(di-tert-butylphosphino)-1',3',5'-triphenyl-1'H-[1,4']-bipyrazole, 2-(di-tert-butylphosphino)-1-phenyl-1H-pyrrole, and 2-(di-tert-butylphosphino)-1-phenyl-1H-indole; bidentate phosphines, such as 1,2-bis(diphenylphosphino)benzene, 2,2'-bis(diphenylphosphino)-1,1'-binaphthyl, 4,5-bis(diphenylphosphino)-9,9-dimethylxanthene, 1,2-bis(diphenylphosphino)ethane, 1,3-bis(diphenylphosphino)propane and 1,1-(diphenylphosphino)ferrocene. Among these, more preferable are 2-di-tert-butylphosphino-2',4',6'-triisopropyl-1,1'-biphenyl, 5-(di-tert-butylphosphino)-1',3',5'-triphenyl-1'H-[1,4']-bipyrazole, 2-di-tert-butylphosphino-2'-(N,N-dimethylamino)biphenyl, 2-(dicyclohexylphosphino)biphenyl, and 2-(di-tert-butylphosphino)-1-phenyl-1H-pyrrole, and most preferable is 2-di-tert-butylphosphino-2', 4',6'-triisopropyl-1,1'-biphenyl.

The N-heterocyclic carbenes are not particularly limited, and examples thereof include 1,3-(bis(2,6-diisopropylphenyl)imidazolinium chloride, 1,3-(bis(2,6-diisopropylphenyl)imidazolium chloride, 1,3-(bis(2,4,6-trimethylphenyl)imidazolinium chloride, 1,3-(bis(2,4,6-trimethylphenyl)imidazolium chloride and the like.

Examples of complexes of transition metal compounds and ligands include palladium complexes. The palladium complexes are not particularly limited, and examples thereof include naphthoquinone-[1,3-bis(diisopropylphenyl)imidazol-2-ylidene]palladium (0), naphthoquinone-[1,3-bis(mesityl)imidazol-2-ylidene]palladium (0), allylchloro-[1,3-bis(diisopropylphenyl)imidazol-2-ylidene]palladium (II), allylchloro-[1,3-bis(diisopropylphenyl)imidazol-2-ylidene]palladium (II), allylchloro-[1,3-bis(mesityl)imidazol-2-ylidene]palladium (II), allylchloro-[1,3-bis(diisopropylphenyl)-2-imidazolidinylidene]palladium (II), phenylallylchloro-[1,3-bis(diisopropylphenyl)imidazol-2-ylidene]palladium (II), phenylallylchloro-[1,3-bis(diisopropylphenyl)-2-imidazolidinylidene]palladium (II), dichloro-[1,3-bis(diisopropylphenyl)imidazol-2-ylidene]palladium (II) dimer, dichloro-(1,2-bis(diphenylphosphino)ferrocenyl)

palladium (II), dichlorobis(tricyclohexylphosphine)palladium (II), dichloro-(1,5-cyclooctadiene)-palladium (II) and the like.

The inert solvents include single or mixed solvents, for example, water; ether solvents such as dioxane, tetrahydrofuran, diethyl ether, diethylene glycol dimethyl ether and ethylene glycol dimethyl ether; aliphatic hydrocarbon solvents such as hexane and heptane; aromatic hydrocarbon solvents such as benzene, toluene and xylene; lower alcohol solvents such as methanol, ethanol, isopropanol and tert-butanol; ketone solvents such as acetone and methyl ethyl ketone; and polar solvents such as N,N-dimethylformamide (DMF), dimethylsulfoxide (DMSO), hexamethylphosphoric acid triamide and acetonitrile. Aromatic hydrocarbon solvents are preferable.

As the basic compounds, a variety of known ones can be used, which include, for example, alkali metal hydroxides such as sodium hydroxide, potassium hydroxide, cesium hydroxide and lithium hydroxide; alkali metal carbonates such as sodium carbonate, potassium carbonate, cesium carbonate and lithium carbonate; alkali metal hydrogencarbonates such as lithium hydrogencarbonate, sodium hydrogencarbonate and potassium hydrogencarbonate; alkali metals such as sodium and potassium; inorganic bases such as sodium amide, sodium hydride and potassium hydride; alkali metal alkoxides such as sodium methoxide, sodium ethoxide, potassium methoxide and potassium ethoxide, lithium tert-butoxide, sodium tert-butoxide, potassium tert-butoxide; and organic bases such as triethylamine, tripropylamine, pyridine, quinoline, piperidine, imidazole, N-ethyldiisopropylamine, dimethylaminopyridine, trimethylamine, dimethylaniline, N-methylmorpholine, 1,5-diazabicyclo[4.3.0]nonene-5 (DBN), 1,8-diazabicyclo[5.4.0]undecene-7 (DBU) and 1,4-diazabicyclo[2.2.2]octane (DABCO).

These basic compounds are used singly or as a mixture of two or more.

More preferable examples are alkali metal alkoxides such as sodium methoxide, sodium ethoxide, potassium methoxide, potassium ethoxide, lithium tert-butoxide, sodium tert-butoxide and potassium tert-butoxide; and alkali metal hydroxides such as sodium hydroxide and potassium hydroxide, or a mixed base of tributylamine and potassium hydroxide.

The amount of transition metal compound used is usually 0.0001 to 1 mol, preferably 0.001 to 0.1 mol per mole of a compound represented by Formula (2).

The amount of ligand used is usually 0.00005 to 10 mol, preferably 0.001 to 0.4 mol per mole of a compound represented by Formula (2). Additionally, the amount of ligand used is usually 0.5 to 10 mol, preferably 1 to 4 mol per mole of a transition metal compound.

The amount of basic compound used is usually 0.5 to 10 mol, preferably 0.5 to 6 mol per mole of a compound represented by Formula (2).

The above reaction may be performed at normal pressure; in an inert gas atmosphere such as nitrogen or argon; or under pressure.

A compound represented by Formula (9) is used in an amount of at least 0.5 mol, preferably about 0.5 to 5 mol per mole of a compound represented by Formula (2).

The reaction temperature of the above reaction is usually room temperature to 200° C., preferably room temperature to 150° C. The reaction time is usually about 1 to 30 hours.

<Step 2>

A compound represented by Formula (11) is prepared by reacting a compound represented by Formula (1) with an organic sulfonic acid.

The reaction of a compound represented by Formula (10) with an organic sulfonic acid is performed without a solvent, or in an inert solvent; and in the presence of a basic compound, or in the absence thereof.

Examples of organic sulfonic acids include methane sulfonic acid, paratoluene sulfonic acid, trifluoromethane sulfonic acid, nitrobenzene sulfonic acid (ortho-, meta-, para-), 2,4,6-trimethylbenzene sulfonic acid and 2,4,6-triisopropylbenzene sulfonic acid. The organic sulfonic acids are preferably used in the form of an acid halide (more preferably, chloride).

An organic sulfonyloxy group represented by $X^3$ is a group derived from an organic sulfonic acid. Examples of organic sulfonyloxy groups include methanesulfonyloxy (mesyloxy), paratoluenesulfonyloxy (tosyloxy), trifluoromethanesulfonyloxy, nitrobenzenesulfonyloxy (ortho-, meta-, para-), 2,4,6-trimethylbenzenesulfonyloxy and 2,4,6-triisopropylbenzenesulfonyloxy.

The inert solvents include single or mixed solvents, for example, water; ether solvents such as dioxane, tetrahydrofuran, cyclopentyl methyl ether, diethyl ether, diethylene glycol dimethyl ether and ethylene glycol dimethyl ether; ester solvents such as methyl acetate, ethyl acetate, isopropyl acetate and t-butyl acetate; aliphatic hydrocarbon solvents such as hexane and heptane; aromatic hydrocarbon solvents such as benzene, toluene and xylene; lower alcohol solvents such as methanol, ethanol, isopropanol and tert-butanol; ketone solvents such as acetone and methyl ethyl ketone; and polar solvents such as N,N-dimethylformamide (DMF), dimethylsulfoxide (DMSO), hexamethylphosphoric acid triamide and acetonitrile. Cyclopentyl methyl ether, ethyl acetate and N,N-dimethylformamide (DMF) are preferable.

As the basic compounds, a variety of known ones can be used, which include, for example, alkali metal hydroxides such as sodium hydroxide, potassium hydroxide, cesium hydroxide and lithium hydroxide; alkali metal carbonates such as sodium carbonate, potassium carbonate, cesium carbonate and lithium carbonate; alkali metal hydrogencarbonates such as lithium hydrogencarbonate, sodium hydrogencarbonate and potassium hydrogencarbonate; alkali metals such as sodium and potassium; inorganic bases such as sodium amide, sodium hydride and potassium hydride; alkali metal alkoxides such as sodium methoxide, sodium ethoxide, potassium methoxide, potassium ethoxide, lithium tert-butoxide, sodium tert-butoxide, potassium tert-butoxide; and organic bases such as triethylamine, tripropylamine, pyridine, quinoline, piperidine, imidazole, N-ethyldiisopropylamine, dimethylaminopyridine, trimethylamine, dimethylaniline, N-methylmorpholine, 1,5-diazabicyclo[4.3.0]nonene-5 (DBN), 1,8-diazabicyclo[5.4.0]undecene-7 (DBU) and 1,4-diazabicyclo[2.2.2]octane (DABCO).

These basic compounds are used singly or as a mixture of two or more.

A basic compound is usually used in an amount of 0.5 to 10 mol, preferably 0.5 to 6 mol per mole of a compound represented by Formula (10).

A sulfonic acid is usually used in an amount of at least 0.5 mol, preferably about 0.5 to 5 mol per mole of a compound represented by Formula (10).

The reaction temperature of the above reaction is usually −20° C. to 100° C., preferably −10° C. to room temperature. The reaction time is usually about 15 minutes to 30 hours.

<Step 3>

A compound represented by Formula (12) is prepared by subjecting a compound represented by Formula (11) to an epoxidation reaction.

The epoxidation reaction is performed without a solvent, or in an inert solvent; and in the presence of a basic compound, or in the absence thereof.

The inert solvents include single or mixed solvents, for example, water; ether solvents such as dioxane, tetrahydrofuran, Cyclopentyl methyl ether, diethyl ether, diethylene glycol dimethyl ether and ethylene glycol dimethyl ether; ester solvents such as methyl acetate, ethyl acetate, isopropyl acetate and t-butyl acetate; aliphatic hydrocarbon solvents such as hexane and heptane; aromatic hydrocarbon solvents such as benzene, toluene and xylene; lower alcohol solvents such as methanol, ethanol, isopropanol and tert-butanol; ketone solvents such as acetone and methyl ethyl ketone; and polar solvents such as N,N-dimethylformamide (DMF), dimethylsulfoxide (DMSO), hexamethylphosphoric acid triamide and acetonitrile. Cyclopentyl methyl ether, methanol and N,N-dimethylformamide (DMF) are preferable.

As the basic compounds, a variety of known ones can be used, which include, for example, alkali metal hydroxides such as sodium hydroxide, potassium hydroxide, cesium hydroxide and lithium hydroxide; alkali metal carbonates such as sodium carbonate, potassium carbonate, cesium carbonate and lithium carbonate; alkali metal hydrogencarbonates such as lithium hydrogencarbonate, sodium hydrogencarbonate and potassium hydrogencarbonate; alkali metals such as sodium and potassium; inorganic bases such as sodium amide, sodium hydride and potassium hydride; alkali metal alkoxides such as sodium methoxide, sodium ethoxide, potassium methoxide, potassium ethoxide, lithium tert-butoxide, sodium tert-butoxide, potassium tert-butoxide; and organic bases such as triethylamine, tripropylamine, pyridine, quinoline, piperidine, imidazole, N-ethyldiisopropylamine, dimethylaminopyridine, trimethylamine, dimethylaniline, N-methylmorpholine, 1,5-diazabicyclo[4.3.0]nonene-5 (DBN), 1,8-diazabicyclo[5.4.0]undecene-7 (DBU) and 1,4-diazabicyclo[2.2.2]octane (DABCO).

These basic compounds are used singly or as a mixture of two or more.

The amount of basic compound used is usually 0.5 to 10 mol, preferably 0.5 to 6 mol per mole of a compound represented by Formula (11).

The above reaction temperature of the above reaction is usually −20° C. to 100° C., preferably 0° C. to room temperature. The reaction time is usually about 15 minutes to 30 hours.

The above reaction may be performed in the presence of a phase-transfer catalyst. Usable phase-transfer catalysts include quaternary ammonium salts substituted by a substituent or substituents selected from the group consisting of linear or branched alkyl groups having 1 to 18 carbon atoms, phenyl lower-alkyl groups and phenyl groups, such as tetrabutylammonium chloride, tetrabutylammonium bromide, tetrabutylammonium fluoride, tetrabutylammonium iodide, tetrabutylammonium hydroxide, tetrabutylammonium hydrogen sulfate, tributylmethylammonium chloride, tributylbenzylammonium chloride, tetrapentylammonium chloride, tetrapentylammonium bromide, tetrahexylammonium chloride, benzyldimethyloctylammonium chloride, methyltrihexylammonium chloride, benzyldimethyloctadecanylammonium chloride, methyltridecanylammonium chloride, benzyltripropylammonium chloride, benzyltriethylammonium chloride, phenyltriethylammonium chloride, tetraethylammonium chloride and tetramethylammonium chloride; phosphonium salts substituted by a linear or branched alkyl groups having 1 to 18 carbon atoms, such as tetrabuthylphosphonium chloride; and pyridinium salts substituted by a linear or branched alkyl groups having 1 to 18 carbon atoms, such as 1-dodecanylpyridinium chloride.

In this case, the reaction is preferably performed in water, or in a mixed solution of water and an organic solvent immiscible with water (benzene, toluene, xylene, methylene chloride, 1,2-dichloroethane, etc.).

The phase-transfer catalyst is usually used in an amount of 0.01 to 0.5 mol, preferably 0.2 to 0.3 mol per mole of a compound represented by Formula (11).

<Step 4>

A compound represented by Formula (13) is prepared by reacting an epoxy compound represented by Formula (12) with a 4-nitroimidazole compound represented by Formula (8).

A compound represented by Formula (12) is usually used in an amount of 0.5 to 5 mol, preferably 0.5 to 3 mol per mole of a compound represented by Formula (8).

As the basic compounds, a variety of known ones can be used, which include, for example, inorganic bases such as metal hydrides, alkali metal lower alkoxides, hydroxides, carbonates and hydrogencarbonates, and organic bases such as acetates.

The metal hydrides are specifically exemplified by sodium hydride and potassium hydride.

The alkali metal lower alkoxides are specifically exemplified by sodium methoxide, sodium ethoxide and potassium tert-butoxide.

The hydroxides are specifically exemplified by sodium hydroxide and potassium hydroxide. The carbonates are specifically exemplified by sodium carbonate and potassium carbonate.

The hydrogencarbonates are specifically exemplified by sodium hydrogencarbonate and potassium hydrogencarbonate.

The inorganic bases also include sodium amides in addition to the above.

The acetates are specifically exemplified by sodium acetate and potassium acetate. The organic salts in addition to the above are specifically exemplified by triethylamine, trimethylamine, diisopropylethylamine, pyridine, dimethylaniline, 1-methylpyrrolidine, N-methylmorpholine, 1,5-diazabicyclo[4.3.0]nonene-5 (DBN), 1,8-diazabicyclo[5.4.0]undecene-7 (DBU) and 1,4-diazabicyclo[2.2.2]octane (DABCO).

The basic compound is used usually in 0.1 to 2 mol, preferably 0.1 to 1 mol, more preferably 0.1 to 0.5 mol per mole of a compound represented by Formula (8).

The reaction of a compound represented by Formula (12) and a compound represented by Formula (8) is performed usually in a suitable solvent.

As the solvents, a variety of known ones can be used. Solvents that do not inhibit the reaction are preferable. Examples of such solvents include aprotic polar solvents such as dimethylformamide (DMF), dimethylsulfoxide (DMSO) and acetonitrile; ketone solvents such as acetone and methyl ethyl ketone; hydrocarbon solvents such as benzene, toluene, xylene, tetralin and liquid paraffin; alcoholic solvents such as methanol, ethanol, isopropanol, n-butanol and tert-butanol; ether solvents such as tetrahydrofuran (THF), cyclopentyl methyl ether, dioxane, diisopropyl ether, diethyl ether and diglyme; ester solvents such as methyl acetate, ethyl acetate, isopropyl acetate and t-butyl acetate; and mixtures thereof. These solvents may contain water.

The reaction of a compound represented by Formula (12) with a compound represented by Formula (8) is performed, for example, by dissolving the compound represented by Formula (8) in a reaction solvent, adding a basic compound to the solution at an ice-cooling temperature or room temperature (e.g., 30° C.) under stirring, stirring the mixture at room temperature to 80° C. for 30 minutes to 1 hour, thereafter adding the compound represented by Formula (12), and continuing stirring the mixture normally at room temperature to 100° C., preferably at 50° C. to 100° C. for 30 minutes to 60 hours, preferably for 1 to 50 hours.

The compound represented by Formula (8) is a known compound, or a compound that can be easily prepared according to a known method.

<Step 5>

A compound represented by Formula (1) is prepared by subjecting a compound represented by Formula (13) to a ring closure reaction.

mole of a compound represented by Formula (8) in the reaction of a compound represented by Formula (12) and the compound represented by Formula (8); and stirring the reaction mixture at 50° C. to 100° C. so as to perform, in a single process, a reaction between the compound represented by Formula (12) and the compound represented by Formula (8), as well as a ring closure reaction of a compound represented by Formula (13) produced by the above reaction.

The compound represented by Formula (10) in Reaction Scheme D above can be produced from the compound represented by Formula (9) using the process shown in Reaction Scheme E below.

Reaction Scheme E

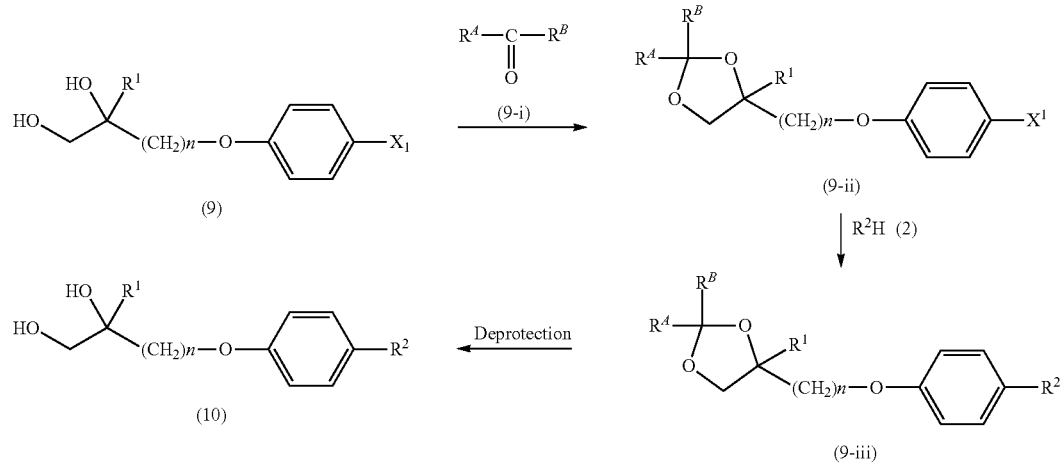

The ring closure reaction is performed by dissolving the compound represented by Formula (13), which is obtained in Step 4, in a reaction solvent, and adding a basic compound thereto and stirring the mixture.

As the reaction solvents and the basic compounds, the same reaction solvents and basic compounds as those used in Step 4 can be used.

The basic compound is usually used in an amount of 1 to an excessive amount, preferably 1 to 5 mol, more preferably 1 to 2 mol per mole of a compound represented by Formula (13).

The reaction temperature of the ring closure reaction is usually 0° C. to 150° C., preferably 0° C. to room temperature. The reaction time is usually 30 minutes to 48 hours, preferably 1 to 24 hours, more preferably 1 to 12 hours.

The reaction mixture may be used in the subsequent ring closure reaction without isolating the compound represented by Formula (13), which is produced in Step (4). A target compound represented by Formula (1) can also be prepared, for example, by reacting a compound represented by Formula (12) with a compound represented by Formula (8) at room temperature to 100° C., then adding a basic compound to the reaction mixture, and further stirring the mixture at 0° C. to 100° C., or by reacting a compound represented by Formula (12) with a compound represented by Formula (8) at room temperature to 100° C., then condensing the reaction mixture, dissolving the residue in a high-boiling point solvent, adding a basic compound to the obtained solution, and further stirring the solution at 0° C. to 100° C.

The target compound represented by Formula (1) can also be prepared by using 0.9 to 2 mol of a basic compound per In the above formulas, $R^1$, $R^2$, $X^1$ and n are the same as the above; $R^A$ is a lower-alkyl group or a phenyl group which may have a substituent or substituents; and $R^B$ is a hydrogen atom or a lower-alkyl group. $R^A$ and $R^B$ may form a cycloalkyl ring together with the carbon atom to which they are bonded.

In Reaction Scheme E, a compound represented by Formula (9) is reacted with a compound represented by Formula (9-i) to obtain a compound represented by Formula (9-ii). Subsequently, the compound represented by Formula (9-ii) is reacted with a compound represented by Formula (2) to obtain a compound represented by Formula (9-iii). Thereafter, the compound represented by Formula (9-iii) is subjected to deprotection to obtain a compound represented by Formula (10).

Examples of lower-alkyl groups represented by $R^A$ and $R^B$ include the aforementioned lower-alkyl groups. Examples of substituents in the phenyl group which may have a substituent or substituents represented by $R^A$ include the aforementioned lower-alkoxy groups. Preferably, 1 to 3 such substituents are present on the phenyl ring.

Examples of cycloalkyl rings that may be formed by $R^A$ and $R^B$ together with the carbon atom to which they are bonded include cyclopentane ring, cyclohexane ring, cycloheptane ring, and the like.

Examples of compounds represented by Formula (9-i) include acetone, benzaldehyde, p-methoxybenzaldehyde, 2,4-dimethoxybenzaldehyde, cyclopentanone, cyclohexanone, cycloheptanone, and the like.

In the reaction of the compound represented by Formula (9) with the compound represented by Formula (9-i), the compound represented by Formula (9-i) is generally used in an amount of 1 to 200 mol, and preferably 1 to 100 mol per mole of the compound represented by Formula (9).

The reaction of the compound represented by Formula (9) with the compound represented by Formula (9-i) is performed in a suitable solvent and in the presence of a suitable acid catalyst.

As the solvents, a wide variety of known ones can be used, and those that do not inhibit the reaction are preferably used. Examples of solvents include aprotic polar solvents such as dimethylformamide (DMF), dimethylsulfoxide (DMSO), and acetonitrile; hydrocarbon solvents such as benzene, toluene, xylene, tetralin, hexane, pentane, and liquid paraffin; ether solvents such as tetrahydrofuran (THF), dioxane, diisopropyl ether, diethyl ether, and diglyme; ester solvents such as methyl acetate, ethyl acetate, isopropyl acetate, and t-butyl acetate; halogenated hydrocarbon solvents such as dichloromethane, and 1,2-dichloroethane; and mixtures thereof. Ketone solvents such as acetone, methyl ethyl ketone, and cyclohexanone are also usable.

Examples of catalysts include inorganic acids such as hydrochloric acid, hydrobromic acid, and sulfuric acid; organic acids such as benzenesulfonic acid, p-toluenesulfonic acid, camphorsulfonic acid, and acetic acid; ammonium salts such as ammonium chloride, pyridinium hexafluoroantimonate; and Lewis acids such as $BF_3 \cdot (OC_2H_5)_2$, titanium tetrachloride, and scandium triflate. These acid catalysts may be used in a common catalytic amount. Specifically, the catalyst is generally used in an amount of 0.01 to 1 mol, and preferably 0.01 to 2 mol per mole of the compound represented by Formula (9).

The reaction is generally performed at 0 to 200° C., and preferably at room temperature to 150° C.; and generally completes in about 30 minutes to about 72 hours.

Two hydroxy groups of the compound represented by Formula (9) are protected by the reaction described above.

The subsequent reaction of the compound represented by Formula (9-ii) with the compound represented by Formula (2) is performed under the same conditions as those for the reaction of the compound represented by Formula (9) with the compound represented by Formula (2) described above.

In the deprotection of the compound represented by Formula (9-iii) thus obtained, various known reaction conditions for removing a protection group from a protected hydroxy group may be employed. For example, the deprotection of the compound represented by Formula (9-iii) is preferably performed in a suitable solvent and in the presence of an acid.

Examples of solvents used in this deprotection include those used in the reaction of the compound represented by Formula (9) with the compound represented by Formula (9-i) described above.

Examples of acids include inorganic acids such as hydrochloric acid, hydrobromic acid, and sulfuric acid; organic acids such as benzenesulfonic acid, p-toluenesulfonic acid, camphorsulfonic acid, and acetic acid; and ammonium salts such as ammonium chloride, and pyridinium hexafluoroantimonate.

The acid is generally used in an amount of 0.01 to 1 mol, and preferably 0.01 to 0.2 mol per mole of the compound represented by Formula (9-iii).

The reaction is generally performed at 0 to 200° C., and preferably at room temperature to 150° C.; and generally completes in about 30 minutes to 24 hours.

The raw material compounds and intended compounds in each of the above reaction formulae, which include the compounds of the present invention, may be in the form of free compounds or salts. Examples of such salts include pharmacologically acceptable salts derived from inorganic bases, organic bases, inorganic acids and organic acids.

The salts of inorganic bases include, for example, metal salts such as alkali metal salts (e.g., lithium salts, sodium salts and potassium salts) and alkaline earth metal salts (e.g. calcium salts and magnesium salts), ammonium salts, salts of alkali metal carbonates (e.g. lithium carbonate, potassium carbonate, sodium carbonate and cesium carbonate), salts of alkali metal hydrogencarbonates (e.g. lithium hydrogencarbonate, sodium hydrogencarbonate and potassium hydrogencarbonate), and salts of alkali metal hydroxides (e.g. lithium hydroxide, sodium hydroxide, potassium hydroxide and cesium hydroxide).

The salts of organic bases include, for example, salts of tri(lower)alkylamine (e.g. trimethylamine, triethylamine and N-ethyldiisopropylamine), pyridine, quinoline, piperidine, imidazole, picoline, dimethylaminopyridine, dimethylaniline, N-(lower)alkylmorpholine (e.g. N-methylmorpholine), 1,5-diazabicyclo[4.3.0]nonene-5 (DBN), 1,8-diazabicyclo[5.4.0]undecene-7 (DBU), and 1,4-diazabicyclo[2.2.2]octane (DABCO).

The salts of inorganic acids include, for example, hydrochlorides, hydrobromides, hydroiodides, sulfates, nitrates and phosphates.

The salts of organic acids include, for example, formates, acetates, propionates, oxalates, malonates, succinates, fumarates, maleates, lactates, malates, citrates, tartrates, carbonates, picrates, methanesulfonates, ethanesulfonates, p-toluenesulfonates and glutamates.

Further, the raw material compounds and intended compounds shown in each of the above reaction formulae, which include the compounds of the present invention, may be in the form of solvates (e.g., hydrates and ethanolates). Preferable solvates include hydrates.

Each target compound obtained in each of the above steps can be isolated and purified from a reaction mixture, for example, by separating a crude reaction product through isolation operations such as filtration, condensation and extraction after a reaction mixture is cooled, and subjecting the separated reaction product to common purification operations such as column chromatography and recrystallization. Conversely, the compounds obtained in each step may also be used as the raw materials in the following step in the form of the reaction mixtures as is, without subjecting them to isolation.

The raw material compounds used in each step described above and the objective compounds may be racemic or optically active isomers, unless otherwise specified. However, in order to obtain an optically active isomer of the compound represented by Formula (1):

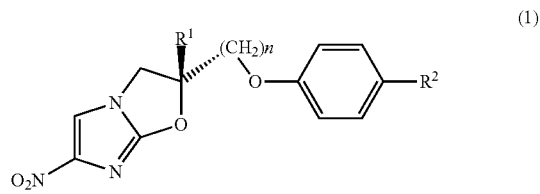

(1)

wherein $R^1$, $R^2$ and n are the same as the above, optically active isomers of the compounds shown below are preferably used.

A compound represented by Formula (9):

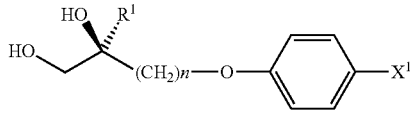
(9)

wherein $R^1$, $X^1$ and n are the same as the above.

A compound represented by Formula (10):

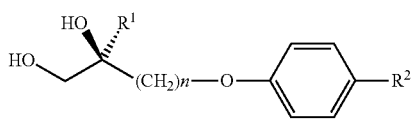
(10)

wherein $R^1$, $R^2$ and n are the same as the above.

A compound represented by Formula (11):

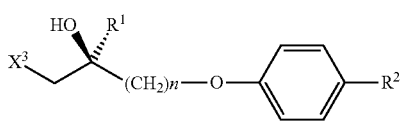
(11)

wherein $R^1$, $R^2$, $X^3$ and n are the same as the above.

A compound represented by Formula (12):

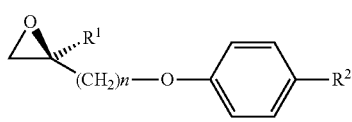
(12)

wherein $R^1$, $R^2$ and n are the same as the above.

A compound represented by Formula (13):

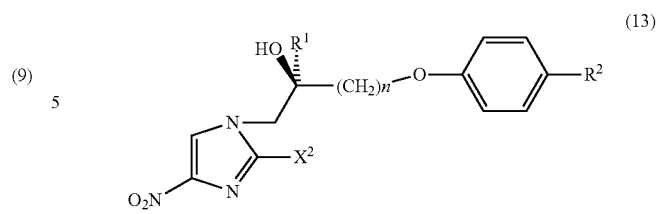
(13)

wherein $R^1$, $R^2$, $X^2$ and n are the same as the above.

Use of the compound represented by Formula (9) in Step 1 enables the optically active isomers of the compounds represented by Formulas (1), and (10)-(13) to maintain their configurations in each step, obtaining the objective compound with a high optical purity.

Advantageous Effects of Invention

The present invention allows a compound represented by Formula (1) to be produced from a compound represented by Formula (2) at a high yield.

According to the present invention, when an optically active isomer is used as the raw material compound, an optically active isomer of the compound represented by Formula (1) can be produced with high optical purity.

According to the research conducted by the present inventors, this is probably because of the reason described below; however, the scope of the present invention is not limited thereby.

Previously known methods include the step in which an R—Ns phenoxide compound starts a nucleophilic attack, as shown in the reaction formula below. In this step, phenoxide attacks the site shown by the arrow path A in the R—Ns compound to obtain the objective R-enantiomer. However, phenoxide also attacks the site shown by the arrow path B, causing the production of S-enantiomer as a byproduct. This reduces the optical purity of the resulting product. In contrast, the method of the present invention does not include the step that causes the reduction of the optical purity; therefore, the method of the present invention is superior to the known methods in this respect.

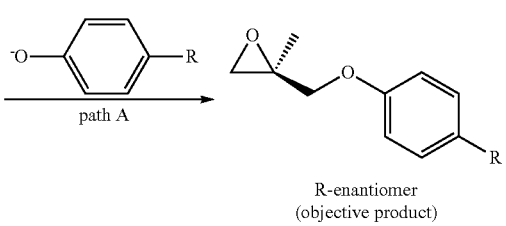

R-enantiomer
(objective product)

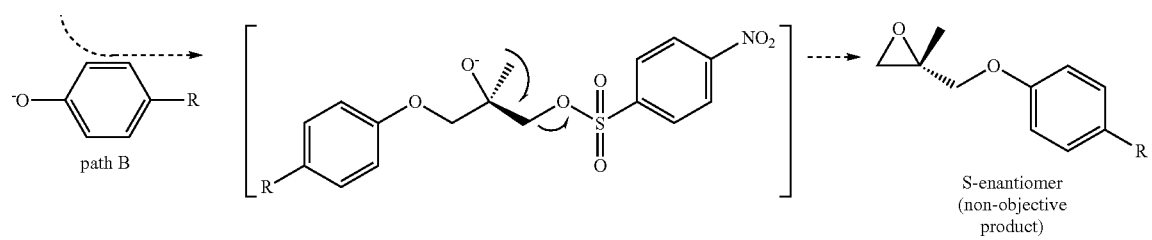

S-enantiomer
(non-objective product)

DESCRIPTION OF EMBODIMENTS

Hereunder, the present invention is explained in detail with reference to Examples.

The abbreviations used hereunder have the meanings usually understood by those having ordinary skill in the art, unless otherwise specified. For example, the abbreviations shown below have the following meanings.

s: singlet, d: doublet, t: triplet, q: quartet, m: multiplet, dd: double doublet, dt: double triplet, br: broad (wide)
aq.: aqueous solution
MeOH: Methanol

REFERENCE EXAMPLE 1

Production of 2-[(4-bromophenoxy)methyl]-2-methyloxirane

4-Bromophenol (80 g, 462 mmol), 2-(chloromethyl)-2-methyloxirane (400 ml) and potassium carbonate (95.86 g, 693 mmol) were mixed and allowed to react at 100° C. for 4 hours. After the reaction was completed, the mixture was concentrated under reduced pressure. Ethyl acetate (200 ml) and water (400 ml) were added thereto, followed by extraction. The water layer was extracted with ethyl acetate (200 ml). The organic layer was washed with water (200 ml) twice. The organic layer was then concentrated under reduced pressure to remove the ethyl acetate. Thereafter, toluene was added and the resulting mixture was concentrated under reduced pressure, obtaining 120 g of crude product.

$^1$H-NMR (300 MHz, CDCl$_3$) δppm: 1.47 (3H, s), 2.73 (1H, d, J=4.8 Hz), 2.86 (1H, d, J=4.8 Hz), 3.90 (1H, d, J=10.7 Hz), 4.02 (1H, d, J=10.7 Hz), 6.80 (2H, dd, J=6.9, 2.3 Hz), 7.37 (2H, dd, J=6.9, 2.3 Hz).

EXAMPLE 1

Production of (R)-3-(4-bromophenoxy)-2-methylpropane-1,2-diol

A mixture of β-methallyl alcohol (90.0 g, 1.25 mol), D-(−)-diisopropyl tartrate (17.53 g, 75.0 mmol), molecular sieves (MS-4A, 45.0 g), and dehydrated toluene (900 ml) was stirred at −18° C. Titanium tetraisopropoxide (17.7 g, 62.4 mmol) was added to the mixture, followed by stirring at −16 to −18° C. for 0.5 hour. Thereafter, 80% cumene hydroperoxide (404 g (total amount), 2.12 mol) was added thereto dropwise at −16 to −18° C. over a period of 2 hours, followed by stirring at −10° C. for 5 hours. Dimethyl sulfoxide (95.7 g, 1,225 mmol) was added thereto at 11 to 13° C. over a period of 0.7 hour. The resulting mixture was stirred at room temperature for 6 hours, and allowed to stand overnight. After adding Celite (18.0 g) and conduction of stirring for 0.5 hour, the reaction mixture was subjected to filtration, obtaining a toluene solution of (S)-2-methylglycidyl alcohol.

4-Bromophenol (108 g, 624 mmol) and a 25% sodium hydroxide aqueous solution (110 g) were added to the toluene solution thus obtained, followed by stirring at 40° C. for 9 hours. After cooling the reaction mixture to room temperature, activated carbon (9.0 g) and Celite (45.0 g) were added thereto. The reaction mixture was then stirred for 0.5 hour and subjected to filtration. The toluene layer was washed with water, and then the toluene and cumyl alcohol were distilled off under reduced pressure. Toluene (162 ml) was added to the concentrated residue, followed by heating to 70° C. to dissolve the concentrated residue. The resulting solution was cooled to room temperature over a period of 5 hours. Hexane (162 ml) was added to the solution, followed by stirring for 5 hours. The precipitated white crystals were collected by filtration, and then washed with a mixed solvent (90 ml) of hexane and toluene (hexane/toluene mixed ratio of 3/1). The crystals were dried by a blower at 50° C., obtaining 123.8 g of the objective product (yield: 76.1% based on 4-bromophenol).

Melting point: 90° C.
Optical purity: 92.2% ee
$^1$H-NMR(CDCl$_3$) δppm: 1.30 (s, 3H), 2.08 (t, J=5.5 Hz, 1H), 2.62 (s, 1H), 3.58 (dd, J=11.2 Hz, JJ=6.1 Hz, 1H), 3.72 (dd, J=8.5 Hz, 2H), 3.90 (q, J=8.5 Hz, 2H), 6.81 (dt, J=9.1 Hz, JJ=2.3 Hz, 2H), 7.39 (dt, J=9.1 Hz, JJ=2.2 Hz, 2H).

EXAMPLE 2

Production of 3-(4-bromophenoxy)-2-methylpropane-1,2-diol

A mixture of β-methallyl alcohol (10 g, 139 mmol) and sodium tungstate dihydrate (92 mg, 0.28 mmol) was stirred at room temperature, and a 35% hydrogen peroxide solution (17.3 g, 153 mmol) was added thereto dropwise over a period of 5 minutes. The mixture was heated to 40° C. and stirred for 7 hours. Potassium carbonate (9.6 g, 69 mmol) and 4-bromophenol (7.9 g, 46 mmol) were added to a half amount of the resulting reaction mixture (70 mmol, based on β-methallyl alcohol), followed by stirring at 60° C. for 2.5 hours. After adding toluene (30 ml), the mixture was heated, washed with water at a temperature about 60° C., and then cooled with ice. The precipitated crystals were collected by filtration, washed with toluene (5 ml), and then dried under reduced pressure, obtaining 9.8 g of 3-(4-bromophenoxy)-2-methylpropane-1,2-diol (yield: 82% (based on 4-bromophenol)).

EXAMPLE 3

Production of 3-(4-bromophenoxy)-2-methylpropane-1,2-diol

2-[(4-Bromophenoxy)methyl]-2-methyloxirane (72.9 g, 300 mmol), acetone (360 ml), water (180 ml), and sulfuric acid (7.3 ml) were mixed and stirred at 60° C. for 1 hour. After cooling, the mixture was concentrated under reduced pressure. Ethyl acetate (360 ml) and a saturated sodium bicarbonate solution were added to the concentrated residue, followed by extraction. Thereafter, the ethyl acetate layer was dried over anhydrous sodium sulfate. Ethyl acetate (102 ml) was added to the resulting crude product and heated to dissolve the crude product. The resulting solution was cooled to room temperature, and then hexane (204 ml) was added thereto, followed by stirring at a temperature 10° C. or less for 1 hour. The precipitated crystals were collected by filtration and then washed with a mixture of ethyl acetate (24 ml) and hexane (48 ml). The resulting crystals were dried under reduced pressure, obtaining 44.0 g of the objective product (yield: 56%).

EXAMPLE 4

Production of (R)-1-[4-(2,3-epoxy-2-methylpropoxy)phenyl]-4-[4-(trifluoromethoxy)phenoxy]piperidine (R)-3-(4-Bromophenoxy)-2-methylpropane-1,2-diol (87.96 g, 336.9 mmol, optical purity of 92.2% ee), 4-[4-(trifluoromethoxy)phenoxy]piperidine (80 g, 306.2 mmol), tris(dibenzylideneacetone)dipalladium (0) (Pd$_2$dba$_3$, 701 mg, 0.77 mmol), 2-di-tert-butylphosphino-2',4',6'-triisopropyl-1,1'-biphenyl (780 mg, 1.84 mmol), sodium tert-butoxide (33.85 g, 352.2 mmol), and toluene (240 ml) were mixed, followed by stirring under an argon atmosphere at 70° C. for 6 hours. After cooling, an ammonium chloride aqueous solution was added to the reaction mixture, followed by extraction with toluene. Thereafter, the organic layer was distilled off under reduced pressure, obtaining a crude product of (R)-2-methyl-3-(4-{4-[4-(trifluoromethoxy)phenoxy]piperidin-1-yl}phenoxy)propane-1,2-diol.

$^1$H-NMR (300 MHz, CDCl$_3$) δppm: 1.28 (3H, s), 1.88-2.03 (2H, m), 2.03-2.19 (2H, m), 2.22 (1H, br. s), 2.75 (1H, br. s), 2.92-3.05 (2H, m), 3.30-3.45 (2H, m), 3.57 (1H, d, J=11.2 Hz), 3.73 (1H, d, J=11.2 Hz), 3.86 (1H, d, J=9.0 Hz), 3.93 (1H, d, J=9.0 Hz), 4.36-4.48 (1H, m), 6.78-6.98 (6H, m), 7.13 (2H, d, J=9.3 Hz).

Ethyl acetate (810 ml) and triethylamine (62 g, 612 mmol) were added to the resulting crude product. Methanesulfonyl chloride (40.3 g, 351.8 mmol) was added thereto while cooling with ice until the starting materials became undetectable, followed by stirring for 20 minutes. After the reaction was completed, water was added to the mixed solution, followed by extraction with ethyl acetate. The ethyl acetate layer was washed with water and then distilled off under reduced pressure, obtaining a crude product of (S)-2-hydroxy-2-methyl-3-(4-{4-[4-(trifluoromethoxy)phenoxy]piperidin-1-yl}phenoxy)propylmethanesulfonate.

$^1$H-NMR (300 MHz, CDCl$_3$) δppm: 1.37 (3H, s), 1.98-2.05 (2H, m), 2.05-2.19 (2H, m), 2.63 (1H, s), 2.93-3.07 (2H, m), 3.03 (3H, s), 3.32-3.43 (2H, m), 3.85 (1H, d, J=9.2 Hz), 3.90 (1H, d, J=9.2 Hz), 4.27 (2H, s), 4.38-4.47 (1H, m), 6.81-6.97 (6H, m), 7.14 (2H, d, J=10.0 Hz).

Methanol (954 ml) and potassium carbonate (84.7 g, 612 mmol) were added to the crude product. The resulting mixture was stirred for 30 minutes at a temperature from 0° C. to room temperature. The reaction mixture was distilled off under reduced pressure, and then toluene and water were added thereto. The toluene layer was washed with water and distilled off under reduced pressure. isopropanol (520 ml) and water (130 ml) were added to the resulting residue and heated to dissolve the residue. The resulting solution was cooled to obtain precipitated crystals. The precipitated crystals thus obtained were collected by filtration and dried, obtaining 98.5 g of (R)-1-{4-[(2,3-epoxy-2-methylpropoxy)phenyl]-4-[4-(trifluoromethoxy)phenoxy]piperidine (yield: 76.2%).

Optical purity: 94.32% ee $^1$H-NMR (300 MHz, CDCl$_3$) δppm: 1.48 (3H, s), 1.9-2.1 (4H, m), 2.72 (1H, d, J=5 Hz), 2.86 (1H, d, J=5 Hz), 2.9-3.1 (2H, m), 3.3-3.5 (2H, m), 3.91 (1H, d, J=10 Hz), 3.98 (1H, d, J=10 Hz), 4.3-4.5 (1H, m), 6.8-7.0 (6H, m), 7.14 (2H, d, J=9 Hz).

EXAMPLE 5

Production of 4-[(4-bromophenoxy)methyl]-2,2,4-trimethyl-1,3-dioxolane 3-(4-Bromophenoxy)-2-methylpropane-1,2-diol (261 mg, 1.00 mmol), acetone (77 mg, 1.3 mmol), tetrahydrofuran (5 mL), and a boron trifluoride diethyl ether complex (3 drops) were mixed. The mixture was stirred at room temperature for 67 hours, and acetone (102 mg, 1.76 mmol) was added thereto, followed by stirring for 2 hours. Sodium carbonate, ethyl acetate, and water were added to the reaction mixture to conduct extraction. The organic layer was washed with a saline solution twice. A residue was obtained by concentrating the organic layer under reduced pressure, and the residue was subjected to chromatography refining (methylene chloride) using silica gel, obtaining 121 mg of the objective compound (yield: 40%).

Property: Colorless Oily Product $^1$H-NMR (CDCl$_3$) δppm: 1.43 (9H, s), 3.74 (1H, d, J=8.6 Hz), 3.78 (1H, d, J=8.6 Hz), 3.84 (1H, d, J=8.8 Hz), 4.11 (1H, d, J=8.8 Hz), 6.78 (2H, d, J=9.0 Hz), 7.36 (2H, d, J=9.0 Hz).

EXAMPLE 6

Production of 4-[(4-bromophenoxy)methyl]-2,2,4-trimethyl-1,3-dioxolane 3-(4-Bromophenoxy)-2-methylpropane-1,2-diol (261 mg, 1.00 mmol), acetone (10 mL), and a boron trifluoride diethyl ether complex (3 drops) were mixed. The mixture was then stirred at room temperature for 14 hours. A residue was obtained by concentrating the mixture under reduced pressure, and ethyl acetate and water were added thereto, followed by extraction. The organic layer was washed with a saline solution twice. A residue was obtained by concentrating the organic layer under reduced pressure, and the resulting residue was then subjected to chromatography refining (methylene chloride) using silica gel, obtaining 183 mg of the objective compound (yield: 61%).

Property: Colorless Oily Product $^1$H-NMR (CDCl$_3$) δppm: 1.43 (9H, s), 3.75 (1H, d, J=8.6 Hz), 3.78 (1H, d, J=8.6 Hz), 3.85 (1H, d, J=8.8 Hz), 4.11 (1H, d, J=8.8 Hz), 6.79 (2H, d, J=9.1 Hz), 7.37 (2H, d, J=9.1 Hz).

EXAMPLE 7

Production of 4-[4-(trifluoromethoxy)phenoxy]-1-{4-[(2,2,4-trimethyl-1,3-dioxolan-4-yl)methoxy]phenyl}piperidine 4-[(4-Bromophenoxy)methyl]-2,2,4-trimethyl-1,3-dioxolane (156 mg, 0.518 mmol), 4-[4-(trifluoromethoxy)phenoxy]piperidine (135 mg, 0.517 mmol), palladium acetate (1.2 mg, 0.0053 mmol), tri-tert-butylphosphine tetraphenylborate (2.7 mg, 0.0052 mmol), sodium tert-butoxide (55 mg, 0.57 mmol), and toluene (2 mL) were mixed and stirred under reflux for 2 hours. Ethyl acetate and water were added to the reaction mixture, followed by extraction. The organic layer was washed with water twice. A residue was obtained by concentrating the organic layer under reduced pressure, and the resulting residue was then subjected to chromatography refining (methylene chloride) using silica gel, obtaining 232 mg of the objective compound (yield: 93%).

Property: Pale Yellow Oily Product $^1$H-NMR (CDCl$_3$) δppm: 1.43 (9H, s), 1.9-2.0 (2H, m), 2.1-2.2 (2H, m), 2.9-3.1 (2H, m), 3.3-3.4 (2H, m), 3.75 (1H, d, J=8.7 Hz), 3.78 (1H, d, J=8.7 Hz), 3.84 (1H, d, J=8.8 Hz), 4.13 (1H, d, J=8.8 Hz), 4.4-4.5 (1H, m), 6.84 (2H, d, J=9.2 Hz), 6.9-7.0 (4H, m), 7.14 (2H, d, J=9.2 Hz).

EXAMPLE 8

Production of 2-methyl-3-(4-{4-[4-(trifluoromethoxy)phenoxy]piperidin-1-yl}phenoxy)propane-1,2-diol 4-[4-(Trifluoromethoxy)phenoxy]-1-{4-[(2,2,4-trimethyl-1,3-dioxolan-4-yl)methoxy]phenyl}piperidine (223 mg, 0.463 mmol), ethanol (10 mL), and concentrated hydrochloric acid (2 mL) were mixed and stirred at room temperature for 14 hours. Water was added to the reaction mixture, followed by neutralization with sodium carbonate. Ethyl acetate was added to the mixture to conduct extraction. The organic layer was washed with water three times. The organic layer was concentrated under reduced pressure, obtaining 196 mg (yield: 96%) of the objective compound.
Property: White Crystal $^1$H-NMR (CDCl$_3$) δppm: 1.27 (3H, s), 1.9-2.0 (2H, m), 2.1-2.2 (2H, m), 2.4 (1H, br. s), 2.8 (1H, br. s), 2.9-3.1 (2H, m), 3.3-3.4 (2H, m), 3.56 (1H, d, J=11.2 Hz), 3.71 (1H, d, J=11.2 Hz), 3.85 (1H, d, J=9.1 Hz), 3.91 (1H, d, J=9.1 Hz), 4.4-4.5 (1H, m), 6.85 (2H, d, J=9.2 Hz), 6.9-7.0 (4H, m), 7.13 (2H, d, J=9.2 Hz).

EXAMPLE 9

Production of (R)-2-methyl-6-nitro-2-{4-[4-(4-trifluoromethoxyphenoxy)piperidin-1-yl]phenoxymethyl}-2,3-dihydroimidazo[2,1-b]oxazole (R)-1-[4-(2,3-epoxy-2-methylpropoxy)phenyl]-4-[4-(trifluoromethoxy)phenoxy]piperidine (10.0 g, 23.6 mmol, optical purity of 94.3% ee), 2-chloro-4-nitroimidazole (4.0 g, 27.2 mmol), sodium acetate (0.4 g, 4.9 mmol), and t-butyl acetate (10 ml) were mixed and stirred at 100° C. for 3.5 hours. Methanol (70 ml) was added to the reaction mixture, and then a 25% sodium hydroxide aqueous solution (6.3 g, 39.4 mmol) was added thereto dropwise while cooling with ice. The resulting mixture was stirred at 0° C. for 1.5 hours, and further stirred at approximately room temperature for 40 minutes. Water (15 ml) and ethyl acetate (5 ml) were added thereto, and the mixture was stirred at 45 to 55° C. for 1 hour. The mixture was cooled to room temperature, and the precipitated crystals were collected by filtration. The precipitated crystals were subsequently washed with methanol (30 ml) and water (40 ml). Methanol (100 ml) was added to the resulting crystals, followed by stirring under reflux for 30 minutes. The mixture was cooled to room temperature. The crystals were then collected by filtration and washed with methanol (30 ml). The resulting crystals were dried under reduced pressure, obtaining 9.3 g of the objective product (yield: 73%).

Optical purity: 99.4% ee.

EXAMPLE 10

Production of 3-(4-chlorophenoxy)-2-methylpropane-1,2-diol

A mixture of β-methallyl alcohol (50 g, 693 mmol) and sodium tungstate dihydrate (460 mg, 1.4 mmol) was stirred at room temperature. A 30% hydrogen peroxide solution (86.5 g, 763 mmol) was added thereto dropwise over a period of 5 minutes. The mixture was heated to 40° C. and stirred for 9 hours. Potassium carbonate (79.7 g, 576 mmol) and 4-chlorophenol (52.4 g, 407 mmol) were added to the resulting reaction mixture, followed by stirring at 70° C. for 1 hour. After adding toluene (390 ml), the mixture was heated and then washed with water at a temperature about 60° C. The reaction mixture was cooled with ice, and then the precipitated crystals were collected by filtration. The resulting crystals were dried under reduced pressure, obtaining 60.0 g of 3-(4-chlorophenoxy)-2-methylpropane-1,2-diol (yield: 68% (based on 4-chlorophenol)).

$^1$H-NMR (300 MHz, CDCl$_3$) δppm: 1.29 (3H, s), 2.29 (1H, br.t, J=5.9 Hz), 2.74 (1H, s), 3.57 (1H, dd, J=11.1, 5.9 Hz), 6.79-6.90 (2H, m), 7.19-7.30 (2H, m).

EXAMPLE 11

Production of 2-methyl-3-(4-{4-[4-(trifluoromethoxy)phenoxy]piperidin-1-yl}phenoxy)propane-1,2-diol 3-(4-Chlorophenoxy)-2-methylpropane-1,2-diol (190.7 mg, 0.88 mmol), 4-[4-(trifluoromethoxy)phenoxy]piperidine (208.9 mg, 0.8 mmol), Pd$_2$dba$_3$ (1.8 mg, 0.002 mmol), 2-di-tert-butylphosphino-2',4',6'-triisopropyl-1,1'-biphenyl (3.4 mg, 0.008 mmol), sodium tert-butoxide (76.9 mg, 0.8 mmol), and toluene (0.6 ml) were mixed. The mixture was stirred under an argon atmosphere at 110° C. for 3 hours. It was confirmed that 2-methyl-3-(4-{4-[4-(trifluoromethoxy)phenoxy]piperidin-1-yl}phenoxy)propane-1,2-diol was produced with the inversion rate of 91% using UPLC.

Analysis conditions (UPLC):
Detector: Ultraviolet absorption detector (measurement wavelength: 220 nm)
Column: ACQUITY UPLC BEH C18 (2.1 mm (inside diameter)×50 mm, 1.7 μm), manufactured by WATERS
Column temperature: 50° C.
Mobile phase: 0.1 M HCOONH$_4$ aq./MeOH
Gradient conditions: The ratio of 0.1 M HCOONH$_4$ aq./MeOH was linearly changed from 70/30 to 20/80 in 3 minutes.

EXAMPLE 12

Production of (R)-2-methyl-3-(4-{4-[4-(trifluoromethoxy)phenoxy]piperidin-1-yl}phenoxy)propane-1,2-diol p-toluenesulfonic acid salt (R)-3-(4-Bromophenoxy)-2-methylpropane-1,2-diol (20.0 kg, 76.6 mol), 4-[4-(trifluoromethoxy)phenoxy]piperidine (22.0 kg, 84.3 mol), tris(dibenzylideneacetone)dipalladium (0) (175 g, 0.19 mol), 2-di-tert-butylphosphino-2',4',6'-triisopropyl-1,1'-biphenyl (195 g, 0.46 mol), sodium tert-butoxide (8.46 kg, 88.0 mol), and toluene (240 ml) were mixed, followed by stirring under an argon atmosphere at 70° C. for 3 hours. After cooling, an ammonium chloride aqueous solution was added to the reaction mixture, followed by extraction with toluene. Isopropanol was flowed therein, and p-toluenesulfonic acid monohydrate (16.0 kg, 84.1 mol) was added thereto, followed by stirring. The precipitated crystals thus obtained were collected by filtration and dried, obtaining 40.3 kg of (R)-2-methyl-3-(4-{4-[4-(trifluoromethoxy)phenoxy]piperidin-1-yl}phenoxy)propane-1,2-diol p-toluenesulfonic acid salt (yield: 85.7%).

EXAMPLE 13

Production of (R)-1-[4-(2,3-epoxy-2-methylpropoxy)phenyl]-4-[4-(trifluoromethoxy)phenoxy]piperidine (R)-2-methyl-3-(4-{4-[4-(trifluoromethoxy)phenoxy]piperidin-1-yl}phenoxy)propane-1,2-diol p-toluenesulfonic acid salt (9 kg, 14.7 mol), cyclopentyl methyl ether (9 L), and triethylamine (4.2 kg, 41.1 mol) were mixed. Thereafter, methanesulfonyl chloride (1.9 kg, 16.8 mol) was added thereto dropwise at a temperature of 5° C. or less. After the reaction was completed, a 25% sodium hydroxide aqueous solution (9 L) was added to the mixture, followed by stirring at a temperature about 40° C. for 90 minutes. Toluene and water were added to the reaction mixture. The toluene layer was washed with water and then distilled off under reduced pressure. 70% isopropanol (63 L) was added to the resulting residue, followed by heating to dissolve the residue. After cooling, precipitated crystals were collected by filtration and dried, obtaining 5.4 kg of (R)-1-[4-(2,3-epoxy-2-methylpropoxy)phenyl]-4-[4-(trifluoromethoxyphenoxy]piperidine (yield: 86.7%).

EXAMPLE 14

Production of (R)-2-methyl-3-(4-{4-[4-(trifluoromethoxy)phenoxy]piperidin-1-yl}phenoxy)propane-1,2-diol (R)-3-(4-Bromophenoxy)-2-methylpropane-1,2-diol (2.0 g, 7.7 mmol), 4-[4-(trifluoromethoxy)phenoxy]piperidine (2.0 g, 7.7 mmol), tris(dibenzylideneacetone)dipalladium (0) (0.141 g, 0.15 mmol), 2-di-tert-butylphosphino-2',4',6'-triisopropyl-1,1'-biphenyl (0.157 g, 0.37 mmol), potassium hydroxide (0.864 g, 15.4 mmol), tributylamine (5 mL), and xylene (46 ml) were mixed, followed by stirring under a nitrogen atmosphere at 80° C. for 6 hours. Using HPLC, it was confirmed that (R)-2-methyl-3-(4-{4-[4-(trifluoromethoxy)phenoxy]piperidin-1-yl}phenoxy)propane-1,2-diol was produced with the inversion rate of 96%.

EXAMPLE 15

Production of (R)-2-methyl-3-(4-{4-[4-(trifluoromethoxy)phenoxy]piperidin-1-yl}phenoxy)propane-1,2-diol (R)-3-(4-Bromophenoxy)-2-methylpropane-1,2-diol (2.0 g, 7.7 mmol), 4-[4-(trifluoromethoxy)phenoxy]piperidine (2.0 g, 7.7 mmol), tris(dibenzylideneacetone)dipalladium (0) (0.141 g, 0.15 mmol), 2-di-tert-butylphosphino-2',4',6'-triisopropyl-1,1'-biphenyl (0.157 g, 0.37 mmol), potassium phosphate (1.88 g, 8.86 mmol), and toluene (46 ml) were mixed, followed by stirring under a nitrogen atmosphere at 80° C. for 21 hours. Using HPLC, it was confirmed that (R)-2-methyl-3-(4-{4-[4-(trifluoromethoxy)phenoxy]piperidin-1-yl}phenoxy)propane-1,2-diol was produced with the inversion rate of 52%.

EXAMPLE 16

Production of (R)-2-methyl-3-(4-{4-[4-(trifluoromethoxy)phenoxy]piperidin-1-yl}phenoxy)propane-1,2-diol (R)-3-(4-Bromophenoxy)-2-methylpropane-1,2-diol (2.0 g, 7.7 mmol), 4-[4-(trifluoromethoxy)phenoxy]piperidine (2.0 g, 7.7 mmol), tris(dibenzylideneacetone)dipalladium (0) (0.141 g, 0.15 mmol), 2-di-tert-butylphosphino-2',4',6'-triisopropyl-1,1'-biphenyl (0.157 g, 0.37 mmol), sodium hydroxide (0.354 g, 8.86 mmol), and toluene (46 ml) were mixed, followed by stirring under a nitrogen atmosphere at 80° C. for 14 hours. Using HPLC, it was confirmed that (R)-2-methyl-3-(4-{4-[4-(trifluoromethoxy)phenoxy]piperidin-1-yl}phenoxy)propane-1,2-diol was produced with the inversion rate of 93%.

EXAMPLE 17

Production of (R)-2-methyl-3-(4-{4-[4-(trifluoromethoxy)phenoxy]piperidin-1-yl}phenoxy)propane-1,2-diol (R)-3-(4-Bromophenoxy)-2-methylpropane-1,2-diol (2.0 g, 7.7 mmol), 4-[4-(trifluoromethoxy)phenoxy]piperidine (2.0 g, 7.7 mmol), tris(dibenzylideneacetone)dipalladium (0) (0.141 g, 0.15 mmol), 2-di-tert-butylphosphino-2',4',6'-triisopropyl-1,1'-biphenyl (0.637 g, 0.15 mmol), cesium carbonate (2.885 g, 8.86 mmol), and toluene (46 ml) were mixed, followed by stirring under a nitrogen atmosphere at 80° C. or 14 hours. Using HPLC, it was confirmed that (R)-2-methyl-3-(4-{4-[4-(trifluoromethoxy)phenoxy]piperidin-1-yl}phenoxy)propane-1,2-diol was produced with the inversion rate of 79%.

EXAMPLE 18

Production of (R)-2-methyl-3-(4-{4-[4-(trifluoromethoxy)phenoxy]piperidin-1-yl}phenoxy)propane-1,2-diol (R)-3-(4-Bromophenoxy)-2-methylpropane-1,2-diol (2.0 g, 7.7 mmol), 4-[4-(trifluoromethoxy)phenoxy]piperidine (2.0 g, 7.7 mmol), tris(dibenzylideneacetone)dipalladium (0) (0.141 g, 0.15 mmol), 2-di-tert-butylphosphino-2'-(N,N-dimethylaminobiphenyl (0.126 g, 0.37 mmol), potassium hydroxide (0.864 g, 15.4 mmol), tributylamine (5 mL), and xylene (46 ml) were mixed, followed by stirring under a nitrogen atmosphere at 80° C. for 21 hours. Using HPLC, it was confirmed that (R)-2-methyl-3-(4-{4-[4-(trifluoromethoxy)phenoxy]piperidin-1-yl}phenoxy)propane-1,2-diol was produced with the inversion rate of 99%.

EXAMPLE 19

Production of (R)-2-methyl-3-(4-{4-[4-(trifluoromethoxy)phenoxy]piperidin-1-yl}phenoxy)propane-1,2-diol (R)-3-(4-Bromophenoxy)-2-methylpropane-1,2-diol (2.0 g, 7.7 mmol), 4-[4-(trifluoromethoxy)phenoxy]piperidine (2.0 g, 7.7 mmol), tris(dibenzylideneacetone)dipalladium (0) (0.141 g, 0.15 mmol), 2-di-tert-butylphosphino-2'-(N,N-dimethylamino)biphenyl (0.126 g, 0.37 mmol), sodium hydroxide (0.354 g, 8.86 mmol), and toluene (46 ml) were mixed, followed by stirring under a nitrogen atmosphere at 80° C. for 14 hours. Using HPLC, it was confirmed that (R)-2-methyl-3-(4-{4-[4-(trifluoromethoxy)phenoxy]piperidin-1-yl}phenoxy)propane-1,2-diol was produced with the inversion rate of 85%.

EXAMPLE 20

Production of (R)-2-methyl-3-(4-{4-[4-(trifluoromethoxy)phenoxy]piperidin-1-yl}phenoxy)propane-1,2-diol (R)-3-(4-Bromophenoxy)-2-methylpropane-1,2-diol (275 mg, 1.05 mmol), 4-[4-(trifluoromethoxy)phenoxy]piperidine (250 mg, 0.96 mmol), tris(dibenzylideneacetone)dipalladium (0) (4.4 mg, 0.0048 mmol), 5-(di-tert-butylphosphino)-1',3',5'-triphenyl-1'H-[1,4']-bipyrazole (5.8 mg, 0.011 mmol), sodium tert-butoxide (106 g, 1.10 mmol), and toluene (0.75 ml) were mixed, followed by stirring under a nitrogen atmosphere at 100° C. for 2 hours. Using HPLC, it was confirmed that (R)-2-methyl-3-(4-{4-[4-(trifluoromethoxy) phenoxy]piperidin-1-yl}phenoxy)propane-1,2-diol was produced with the inversion rate of 99%.

EXAMPLE 21

Production of (R)-2-methyl-3-(4-{4-[4-(trifluoromethoxy)phenoxy]piperidin-1-yl}phenoxy)propane-1,2-diol (R)-3-(4-Bromophenoxy)-2-methylpropane-1,2-diol (275 mg, 1.05 mmol), 4-[4-(trifluoromethoxy)phenoxy]piperidine (250 mg, 0.96 mmol), tris(dibenzylideneacetone)dipalladium (0) (4.4 mg, 0.0048 mmol), 2-(di-tert-butylphosphino)-1-phenyl-1H-pyrrole (3.3 mg, 0.011 mmol), sodium tert-butoxide (106 g, 1.10 mmol), and toluene (0.75 ml) were mixed, followed by stirring under a nitrogen atmosphere at 100° C. for 2 hours. Using HPLC, it was confirmed that (R)-2-methyl-3-(4-{4-[4-(trifluoromethoxy)phenoxy]piperidin-1-yl}phenoxy)propane-1,2-diol was produced with the inversion rate of 93%.

EXAMPLE 22

Production of (R)-2-methyl-3-(4-{4-[4-(trifluoromethoxy)phenoxy]piperidin-1-yl}phenoxy)propane-1,2-diol (R)-3-(4-Bromophenoxy)-2-methylpropane-1,2-diol (275 mg, 1.05 mmol), 4-[4-(trifluoromethoxy)phenoxy]piperidine (250 mg, 0.96 mmol), tris(dibenzylideneacetone)dipalladium (0) (4.4 mg, 0.0048 mmol), 2-(di-tert-butylphosphino)-1-phenyl-1H-indole (3.9 mg, 0.011 mmol), sodium tert-butoxide (106 g, 1.10 mmol), and toluene (0.75 ml) were mixed, followed by stirring under a nitrogen atmosphere at 100° C. for 2 hours. Using HPLC, it was confirmed that (R)-2-methyl-3-(4-{4-[4-(trifluoromethoxy)phenoxy]piperidin-1-yl}phenoxy)propane-1,2-diol was produced with the inversion rate of 89%.

EXAMPLE 23

Production of (R)-2-methyl-3-(4-{4-[4-(trifluoromethoxy)phenoxy]piperidin-1-yl}phenoxy)propane-1,2-diol (R)-3-(4-Bromophenoxy)-2-methylpropane-1,2-diol (275 mg, 1.05 mmol), 4-[4-(trifluoromethoxy)phenoxy]piperidine (250 mg, 0.96 mmol), tris(dibenzylideneacetone)dipalladium (0) (4.4 mg, 0.0048 mmol), 2-(di-tert-butylphosphino)-1,1'-binaphthyl (4.6 mg, 0.011 mmol), sodium tert-butoxide (106 g, 1.10 mmol), and toluene (0.75 ml) were mixed, followed by stirring under a nitrogen atmosphere at 100° C. for 2 hours. Using HPLC, it was confirmed that (R)-2-methyl-3-(4-{4-[4-(trifluoromethoxy)phenoxy]piperidin-1-yl}phenoxy)propane-1,2-diol was produced with the inversion rate of 96%.

EXAMPLE 24

Production of (S)-4-(4-bromophenoxy)methyl-2,2,4-trimethyl-1,3-dioxolane (R)-3-(4-Bromophenoxy)-2-methylpropane-1,2-diol (25 g, 0.1 mol) and p-toluenesulfonic acid (0.91 g, 4.8 mmol) were dissolved in acetone (300 g), followed by stirring under reflux for 5.5 hours. The progress of reaction was monitored by TLC. The generated water was removed by azeotropic distillation with 300 g of solvent under atmospheric pressure, and 300 g of acetone was added during the reaction. After the reaction was completed, the solvent was removed under a reduced pressure and the resulting concentrated residue was dissolved in isopropyl acetate (250 mL). The organic layer thus obtained was washed with a 1 M sodium hydroxide aqueous solution (100 mL). Thereafter, the organic layer was concentrated and dried, obtaining 25 g of (S)-4-(4-bromophenoxy)methyl-2,2,4-trimethyl-1,3-dioxolane (yield: 82%).

EXAMPLE 25

Production of (S)-4-[4-(trifluoromethoxy)phenoxy]-1-{4-[(2,2,4-trimethyl-1,3-dioxolane-4-1y)methoxy]phenyl}piperidine (S)-4-(4-Bromophenoxy)methyl-2,2,4-trimethyl-1,3-dioxolane (2.32 g, 7.7 mmol), 4-[4-(trifluoromethoxy)phenoxy]piperidine (2.0 g, 7.7 mmol), tris(dibenzylideneacetone)dipalladium (0) (0.141 g, 0.15 mmol), 2-dicyclohexylphosphino-2'-(N,N-dimethylamino)biphenyl (0.145 g, 0.37 mmol), potassium hydroxide (0.864 g, 15.4 mmol), tributylamine (5 mL), and xylene (46 ml) were mixed, followed by stirring under a nitrogen atmosphere at 80° C. for 8 hours. Using HPLC, it was confirmed that (S)-4-[4-(trifluoromethoxy)phenoxy]-1-{4-[(2,2,4-trimethyl-1,3-dioxolane-4-1y)methoxy]phenyl}piperidine was produced with the inversion rate of 99%.

EXAMPLE 26

Production of (S)-4-[4-(trifluoromethoxy)phenoxy]-1-{4-[(2,2,4-trimethyl-1,3-dioxolane-4-1y)methoxy]phenyl}piperidine (S)-4-((4-bromophenoxy)methyl)-2,2,4-trimethyl-1,3-dioxolane (2.32 g, 7.7 mmol), 4-[4-(trifluoromethoxy)phenoxy]piperidine (2.0 g, 7.7 mmol), tris(dibenzylideneacetone)dipalladium (0) (0.141 g, 0.15 mmol), 2-dicyclohexylphosphino-1,1'-biphenyl (0.130 g, 0.37 mmol), potassium hydroxide (0.864 g, 15.4 mmol), tributylamine (5 mL), and xylene (46 ml) were mixed, followed by stirring under a nitrogen atmosphere at 80° C. for 8 hours. Using HPLC, it was confirmed that (S)-4-[4-(trifluoromethoxy)phenoxy]-1-{4-[(2,2,4-trimethyl-1,3-dioxolane-4-1y)methoxy]phenyl}piperidine was produced with the inversion rate of 99%.

EXAMPLE 27

Production of (S)-4-[4-(trifluoromethoxy)phenoxy]-1-{4-[(2,2,4-trimethyl-1,3-dioxolane-4-1y)methoxy]phenyl}piperidine (S)-4-((4-Bromophenoxy)methyl)-2,2,4-trimethyl-1,3-dioxolane (287 mg, 1 mmol), 4-[4-(trifluoromethoxy)phenoxy]piperidine (261 mg, 1 mmol), palladium acetate (II) (2.2 mg, 0.01 mmol), 2-dicyclohexylphosphino-2',6'-dimethoxy-1,1'-biphenyl (12.3 mg, 0.03 mmol), sodium tert-butoxide (106 mg, 1.1 mmol), and toluene (1.3 ml) were mixed, followed by stirring under reflux under a nitrogen atmosphere for 8 hours. Using NMR, it was confirmed that (S)-4-[4-(trifluoromethoxy)phenoxy]-1-{4-[(2,2,4-trimethyl-1,3-dioxolane-4-1y)methoxy]phenyl}piperidine was produced with the inversion rate of 99% or more.

EXAMPLE 28

Production of (R)-3-(4-bromophenoxy)-2-methylpropane-1,2-diol

A mixture of β-methallyl alcohol (90.0 g, 1.25 mol), D-(−)-diisopropyl tartrate (17.5 g, 74.8 mmol), molecular sieves 4A (45.0 g), and dehydrated toluene (450 ml) was stirred under a nitrogen atmosphere at −20° C. Titanium tetraisopropoxide (17.7 g, 62.4 mmol) was added thereto over a period of 5 minutes, followed by stirring for 0.5 hour. Thereafter, 80% cumene hydroperoxide (309 g, 1.62 mol) was added thereto dropwise at −20 to -15° C. over a period of 2 hours, followed by stirring at −10° C. for 3 hours. Dimethyl sulfoxide (59.2 g, 748 mmol) was added thereto dropwise at 20 to 35° C. over a period of 0.5 hour. The resulting mixture was stirred at 30 to 40° C. for 3 hours. The mixture was allowed to cool and then to stand overnight. After adding Celite (18 g), the mixture was subjected to filtration, obtaining a toluene solution of (S)-2-methylglycidyl alcohol.

4-Bromophenol (127 g, 734 mmol) and a 10% sodium hydroxide aqueous solution (176 g, 440 mmol) were added to the toluene solution thus obtained, followed by stirring at 55° C. for 5 hours. The mixture was allowed to cool and then to stand overnight. After cooling the mixture to 12° C., 10% diluted sulfuric acid (2.17 N, 423 ml) was added thereto, followed by stirring for 0.2 hour. The toluene layer was separated, and then washed with a 5% sodium hydroxide aqueous solution (178 ml), a 5% saline solution (128 ml, 3 times) and water (128 ml, twice). Thereafter, toluene and cumyl alcohol (cumyl alcohol: Bp 60 to 65° C./2 mmHg) were removed from the organic layer by distillation under reduced pressure. The residue was cooled to 70° C. and toluene (191 ml) was added thereto. The resulting mixture was cooled to 5° C. The precipitated crystals were collected by filtration and then washed with cooled toluene (95 ml).

The crystals thus obtained were dried by a blower, obtaining 154.0 g of (R)-3-(4-bromophenoxy)-2-methylpropane-1, 2-diol (yield: 80.3%, based on 4-bromophenol).

Optical purity: 88.6% ee.
Melting point: 87-89° C.

The invention claimed is:
1. A compound represented by Formula (11):

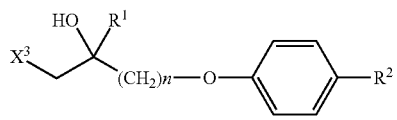
(11)

wherein $R^1$ is a hydrogen atom or lower-alkyl group;
$R^2$ is a 1-piperidyl group substituted at the 4-position with a substituent selected from
(A1a) a phenoxy group substituted on the phenyl moiety with one or more halogen-substituted lower-alkoxy groups,
(A1b) a phenoxy-substituted lower-alkyl group substituted on the phenyl moiety with one or more halogen-substituted lower-alkyl groups,
(A1c) a phenyl-substituted lower-alkoxy lower-alkyl group substituted on the phenyl moiety with halogen,
(A1d) a phenyl-substituted lower-alkyl group substituted on the phenyl moiety with one or more halogen-substituted lower-alkoxy groups,
(A1e) an amino group substituted with a phenyl group substituted with one or more halogen-substituted lower-alkoxy groups, and a lower-alkyl group, and
(A1f) a phenyl-substituted lower-alkoxy group substituted on the phenyl moiety with one or more halogen-substituted lower-alkoxy groups;
n is an integer from 1 to 6; and
$X^3$ is an organic sulfonyloxy group.
2. A method for producing the compound of claim 1,
the method comprising reacting a compound represented by Formula (10):

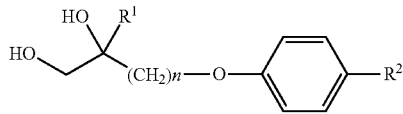
(10)

wherein $R^1$, $R^2$ and n are the same as defined in claim 1, with an organic sulfonic acid.
3. A compound represented by Formula (10):

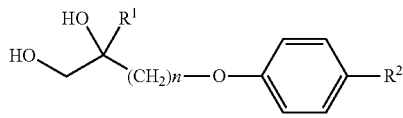
(10)

wherein $R^1$, $R^2$ and n are the same as defined in claim 1.
4. A method for producing the compound of claim 3,
the method comprising reacting a compound represented by Formula (9):

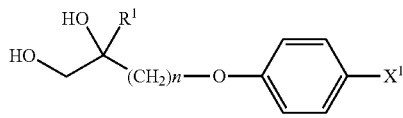
(9)

wherein $X^1$ is a leaving group, and $R^1$ and n are the same as defined in claim 3, with a compound represented by Formula (2):

(2)

wherein $R^2$ is the same as defined in claim 3.
5. A method for producing the compound of claim 3,
the method comprising reacting a compound represented by Formula (9):

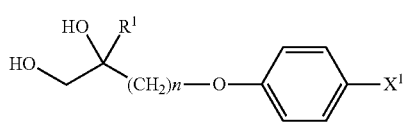
(9)

wherein $X^1$ is a leaving group, and $R^1$ and n are the same as defined in claim 3, with a compound represented by Formula (9-i):

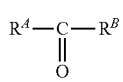
(9-i)

wherein $R^A$ is a lower-alkyl group or a phenyl group which may have a substituent or substituents; and $R^B$ is a hydrogen atom or a lower-alkyl group, $R^A$ and $R^B$ may form a cycloalkyl ring together with the carbon atom to which they are bonded, to obtain a compound represented by Formula (9-ii):

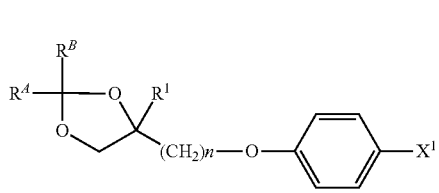
(9-ii)

wherein $R^1$, $X^1$, n, $R^A$ and $R^B$ are the same as the above, the compound represented by Formula (9-ii) is reacted with a compound represented by Formula (2):

(2)

wherein $R^2$ is the same as defined in claim 3,
to obtain a compound represented by Formula (9-iii):

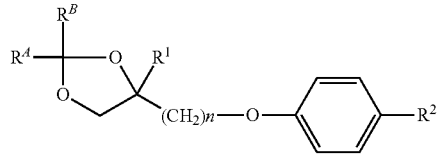
(9-iii)

wherein $R^1$, $R^2$, n, $R^A$ and $R^B$ are the same as the above, and
subjecting the compound represented by Formula (9-iii) to deprotection.

6. A method for producing a compound represented by Formula (12):

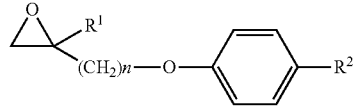
(12)

wherein $R^1$, $R^2$ and n are the same as defined in claim 1,
the method comprising subjecting the compound of claim 1 to an epoxidation reaction.

7. A method for producing a compound represented by Formula (1):

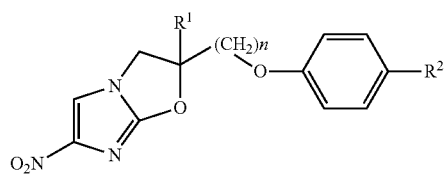
(1)

wherein $R^1$, $R^2$ and n are the same as defined in claim 1,
the method comprising the steps (a) to (c):
(a) subjecting the compound of claim 1 to an epoxidation reaction to prepare a compound represented by Formula (12):

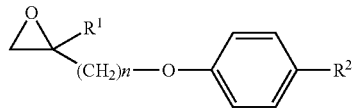
(12)

wherein $R^1$, $R^2$ and n are the same as defined in claim 1;
(b) reacting a compound represented by Formula (12) with a compound represented by Formula (8):

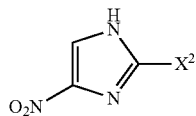
(8)

wherein $X^2$ is a halogen atom, to prepare a compound represented by Formula (13):

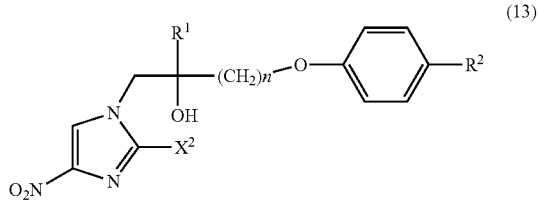
(13)

wherein $R^1$, $R^2$, $X^2$ and n are the same as the above; and
(c) subjecting the compound represented by Formula (13) to a ring closure reaction to prepare the compound represented by Formula (1).

\* \* \* \* \*